US011306289B2

(12) United States Patent
Yee

(10) Patent No.: US 11,306,289 B2
(45) Date of Patent: Apr. 19, 2022

(54) METHODS OF USING IL-21 FOR ADOPTIVE IMMUNOTHERAPY AND IDENTIFICATION OF TUMOR ANTIGENS

(71) Applicant: Fred Hutchinson Cancer Research Center, Seattle, WA (US)

(72) Inventor: Cassian Yee, Seattle, WA (US)

(73) Assignee: Fred Hutchinson Cancer Research Center, Seattle, WA (US)

( * ) Notice: Subject to any disclaimer, the term of this patent is extended or adjusted under 35 U.S.C. 154(b) by 591 days.

(21) Appl. No.: 15/926,874

(22) Filed: Mar. 20, 2018

(65) Prior Publication Data

US 2019/0316088 A1 Oct. 17, 2019

Related U.S. Application Data

(63) Continuation of application No. 14/468,326, filed on Aug. 25, 2014, now Pat. No. 9,951,310, which is a continuation of application No. 12/617,018, filed on Nov. 12, 2009, now abandoned, which is a continuation of application No. 11/285,970, filed on Nov. 23, 2005, now abandoned.

(60) Provisional application No. 60/630,727, filed on Nov. 24, 2004.

(51) Int. Cl.
G01N 33/68 (2006.01)
C12N 5/0783 (2010.01)
G01N 33/50 (2006.01)
G01N 33/574 (2006.01)
A61K 35/17 (2015.01)

(52) U.S. Cl.
CPC ............ *C12N 5/0638* (2013.01); *A61K 35/17* (2013.01); *C12N 5/0636* (2013.01); *G01N 33/505* (2013.01); *G01N 33/5047* (2013.01); *G01N 33/574* (2013.01); *G01N 33/57484* (2013.01); *G01N 33/57492* (2013.01); *G01N 33/6863* (2013.01); *C12N 2501/23* (2013.01); *C12N 2501/2321* (2013.01); *C12N 2502/1121* (2013.01)

(58) Field of Classification Search
None
See application file for complete search history.

(56) References Cited

U.S. PATENT DOCUMENTS

| 5,766,920 A | 6/1998 | Babbitt et al. |
| 5,827,642 A | 10/1998 | Riddell et al. |
| 6,307,024 B1 | 10/2001 | Novak et al. |
| 6,316,257 B1 | 11/2001 | Flyer et al. |
| 9,809,797 B2 | 11/2017 | Yee et al. |
| 9,907,820 B2 | 3/2018 | Cooper et al. |
| 9,951,310 B2 | 4/2018 | Yee |
| 10,072,246 B2 | 9/2018 | Yee et al. |
| 11,098,284 B2 | 8/2021 | Yee et al. |
| 2001/0031253 A1 | 10/2001 | Gruenberg |
| 2002/0119121 A1 | 8/2002 | Vitiello et al. |
| 2003/0108549 A1* | 6/2003 | Carter ............... A61K 38/1793 424/145.1 |
| 2003/0147869 A1 | 8/2003 | Riley et al. |
| 2004/0009150 A1 | 1/2004 | Nelson et al. |
| 2006/0051866 A1 | 3/2006 | Symonds et al. |
| 2006/0121005 A1 | 6/2006 | Berenson et al. |
| 2006/0269973 A1 | 11/2006 | Yee et al. |
| 2009/0221077 A1 | 9/2009 | Ideno et al. |
| 2010/0310533 A1 | 12/2010 | Yee et al. |
| 2016/0175358 A1 | 6/2016 | Jakobovits et al. |
| 2019/0119639 A1 | 4/2019 | Oelke et al. |
| 2019/0316088 A1 | 10/2019 | Yee |

FOREIGN PATENT DOCUMENTS

| EP | 1795599 A1 | 6/2007 |
| EP | 3773626 A1 | 2/2021 |
| WO | 2003-103589 | 12/2003 |
| WO | 2006-063301 | 6/2006 |
| WO | 2006065495 A2 | 6/2006 |
| WO | 2018202808 A2 | 11/2018 |
| WO | 2019/191501 A1 | 10/2019 |

OTHER PUBLICATIONS

Nolte et al. (Journal of Immunotherapy 26(3):257-269 © 2003). (Year: 2003).*
Yee et al. (Methods Mol Med. 2001;61:353-62). (Year: 2001).*
Valmori, et al., "Naturally Occurring Human Lymphocyte Antigen-A2 Restricted CD8 T-Cell Response to the Cancer Testis Antigen Ny-ESO-1 in Melanoma Patients," Cancer Research, (2000), vol. 60: 4499-4506.
Comes, et al., "CD25 Regulatory T Cell Depletion Augments Immunotherapy of Micrometastases by an IL-21-Secreting Cellular Vaccine," J Immunol, (2006), vol. 176: 1750-1758.
Boettler, et al., "T cells with a CD4+CD25+ Regulatory Phenotype Suppress In Vitro Proliferation of Virus-Specific CD8+ T cells during Chronic Hepatitis C Virus Infection," J. Virol., (2005), vol. 79, No. 12: 7860-7867.
Cooper, et al., "Manufacturing of gene-modified cytotoxic T lymphocytes for autologous cellular therapy for lymphoma," Cytotherapy, (2006), vol. 8, No. 2:105-117.

(Continued)

*Primary Examiner* — Zachary S Skelding
(74) *Attorney, Agent, or Firm* — McBee Moore & Vanik IP, LLC

(57) ABSTRACT

Methods for preparing ex vivo T cell cultures using IL-21 compositions for use in adoptive immunotherapy are described. Addition of IL-21 to cultures of non-terminally differentiated T cells population, either isolated or present in peripheral blood mononuclear cells are exposed to one or more tumor antigens, and in the presence of IL-21 compositions and antigen presenting cells (APCs), the resulting T cell population has an enhanced antigen-specificity, and can be reintroduced into the patient. Methods are also disclosed for identifying tumor antigens by culturing T cell populations exposed to IL-21 compositions and APCs in the presence of tumor material.

9 Claims, 13 Drawing Sheets
Specification includes a Sequence Listing.

(56) References Cited

OTHER PUBLICATIONS

Feuerer, et al., "Foxp3+ regulatory T cells: differentiation, specification, subphenotypes," Nature Immunol., (2009), vol. 10, No. 7: 689-695.

Hinrichs, et al., "IL-2 and IL-21 confer opposing differentiation programs to CD8+ T cells for adoptive immunotherapy," Blood, (2008), vol. 111: 5326-5333.

Kaka, et al., "IL-21 gene modified T antigen presenting cells enhance the generation of tumor-specific cytotoxic T lymphocytes with a memory phenotype," Blood, (2006), vol. 108, No. 11, Part 1: 1059A-1060A. Abstract Only.

Li, et al., "IL-21-mediated Foxp3 suppression leads to enhanced generation of antigen-specific CD8+ cytotoxic T lymphocytes," Blood, (2008), vol. 111, No. 1: 229-235.

Nair, et al., "Vaccination against the Forkhead Family Transcription Factor Foxp3 Enhances Tumor Immunity," Cancer Research, (2007), vol. 67, No. 1: 371-380.

Onoda, et al., "Human CD4+ central and effector memory T cells produce IL-21: effect on cytokine-driven proliferation of CD4+ T cell subsets," International Immunol., (2007), vol. 19, No. 10: 1191-1199.

Peng, et al., "Increased tumor-infiltrating CD8+Foxp3+ T lymphocytes are associated with tumor progression in human gastric cancer," Cancer Immunol Immunother, (2012), vol. 61: 2183-2192.

Powell, et al., "Large-scale Depletion of CD25+ Regulatory T Cells from Patient Leukapheresis Samples," J Immunother, (2005), vol. 28, No. 4: 403-411.

Straathof, E al., "An inducible caspase 9 safety switch for T-cell therapy," Blood, (2005), vol. 105: 4247-4254.

Zhao, et al., "Interleukin-21 up-regulates interieukin-21R expression and interferon gamma production by CD8+ cells in SHIV-infected macaques," Exp Biol Med, (2013), vol. 238: 400.

Bisset et al., "Reference values for peripheral blood lymphocyte phenotypes applicable to the healthy adult population in Switzerland," Eur J Haematol, 72:203-212, 2004.

Brentjens et al., "Eradication of systemic B-cell tumors by genetically targeted human T lymphocytes co-stimulated by CD80 and interleukin-15," Nature Medicine, 9(3):279-286, 2003.

Chapuis et al., "Transferred melanoma-specific CD8+ T cells persist, mediate tumor regression, and acquire central memory phenotype," Proc Natl Acad Sci USA, 109(12)4592-4597, 2012.

Comoli et al., "Infusion of autologous Epstein-Barr virus (EBV)-specific cytotoxic T cells for prevention of EBY-related lymphoproliferative disorder in solid organ transplant recipients with evidence of active virus replication," Blood, 99(7):2592-2598, 2002.

Cui et al., "Cytokine genetic adjuvant facilitates prophylactic intravascular DNA vaccine against acute and latent herpes simplex virus infection in mice," Gene Therapy, 12:160-168, 2005.

Foster et al., "Ex-vivo uses and applications of cytokines for adoptive immunotherapy in cancer," Current Pharmaceutical Design, 10(11): 1207-1220, 2004.

Hernandez et al., "The use of HLA A2. I/p53 peptide tetramers to visualize the impact of self tolerance on the TCR repertoire," J Immunol., 164:596-602, 2000.

Hersey et al., "Phase I/II study of immunotherapy with T-cell peptide epitopes in patients with stage IV melanoma," Cancer Immunology, Immunotherapy, 54(3):208-218, 2005.

Hughes et al., "Interleukin 21 efficacy in a mouse model of metastatic renal cell carcinoma," J Clin. Oncology, 22(14S):2598, 2004.

Hughes et al., "Mechanisms of IL-21 enhancement of rituximab efficacy in a lymphoma xenograft model," Poster Session 558-1, Blood, 104(1 I):394A, 2004.

Jin et al., "Distinct activation signals determine whether IL-21 induces B cell costimulation, growth arrest, or Bim-dependent apoptosis," J Immunol., 173:657-665, 2004.

Kasaian et al., "IL-21 limits NK cell responses and promotes antigen-specific T cell activation: a mediator of the transition from innate to adaptive immunity," Immunity, 16:559-569, 2002.

Kindsvogel et al., "IL-21 enhances rituximab-mediated killing of B-lymphoma cell lines in vitro and in vivo," J Clin. Oncology, 22(14S):2581, 2004.

Kurokawa et al., "Induction and clonal expansion of tumor-specific cytotoxic T lymphocytes from renal cell carcinoma patients after stimulation with autologous dendritic cells loaded with tumor cells," Int. J Cancer, 91:749-756, 2001.

Li and Yee, "Cytokine modulation facilitates the in vitro generation of antigen specific T cells for adoptive immunotherapy," Journal of Immunotherapy, 27(6):S2-S3, 2004.

Li et al., "IL-21 influences the frequency, phenotype, and affinity of the antigen-specific CD8 T-cell response," J Immunol., 175:2261-2269, 2005.

Li et al., "Important role ofIL-21 in the generation of human antigen-specific CD8 T cells," Journal of Immunotherapy, 28(6):623, 2005.

Ma et al., "IL-21 activates both innate and adaptive immunity to generate potent antitumor responses that require perforin but are independent ofIFN-y," J Immunol., 171:608-615, 2003.

Maus et al., "Ex vivo expansion of polyclonal and antigen-specific cytotoxic T lymphocytes by artificial APCs expressing ligands for the T-cell receptor, CD28 and 4-IBB," Nat Biotechnol., 20(2): 143-148, 2002.

Mestas et al., "Of mice and not men: differences between mouse and human immunology," J Immunol., 172:2731-2738, 2004.

Moroz et al., "IL-21 enhances and sustains CD8+ T cell responses to achieve durable tumor immunity: comparative evaluation ofIL-2, IL-15, and IL-21," The Journal of Immunology, 173:900-909, 2004.

O'Connell et al., "Elucidating the elite: mechanisms of control in HIV-1 infection," Trends Pharmacol Sci., 30(12):631-637, 2009.

Office Action issued in Canadian Application No. 2,587,136, dated Jul. 24, 2012.

Office Action issued in European Application No. 05 852 204.6, dated Oct. 18, 2011.

Office Action issued in European Application No. 05 852 204.6, dated Aug. 6, 2013.

Office Action issued in European Application No. 05 852 204.6, dated Mar. 31, 2015.

Office Action issued in Japanese Application No. 2007-543536, dated Jun. 20, 2012, and English language translation thereof.

Office Action issued in Japanese Application No. 2007-543536, dated Jun. 1, 2011, and English language translation thereof.

Office Action issued in U.S. Appl. No. 11/285,970, dated Apr. 1, 2008.

Office Action issued in U.S. Appl. No. 11/285,970, dated Jul. 9, 2008.

Office Action issued in U.S. Appl. No. 11/285,970, dated May 12, 2009.

Office Action issued in U.S. Appl. No. 12/617,018, dated Feb. 24, 2014.

Office Action issued in U.S. Appl. No. 12/617,018, dated Jun. 29, 2011.

Office Action issued in U.S. Appl. No. 12/617,018, dated May 18, 2012.

Office Action issued in U.S. Appl. No. 12/617,018, dated Sep. 22, 2011.

Parrish-Novak et al., "Interleukin 21 and its receptor are involved in NK cell expansion and regulation of lymphocyte function," Nature, 408(6808):57-63, 2000.

Parrish-Novak et al., "Interleukin-21 and the IL-21 receptor: novel effectors of NK and T cell responses," J Leukoc. Biol., 72:856-863, 2002.

PCT International Preliminary Report on Patentability issued in PCT Application No. PCT/US2005/042782, dated May 30, 2007.

PCT International Search Report and Written Opinion issued in PCT Application No. PCT/US2005/042782, dated Jul. 24, 2006.

Powell et al., "Transition of late-stage effector T cells to CD27+ CD28+ tumor-reactive effector memory T cells in humans after adoptive cell transfer therapy," Blood, 105(1):241-250, 2004.

Savoldo et al., "Generation of autologous Epstein-Barr virus-specific cytotoxic T cells for adoptive immunotherapy in solid organ transplant recipients," Transplantation, 72(6): 1078-1086, 2001.

(56) References Cited

OTHER PUBLICATIONS

Sivakumar et al., "Interleukin-21 is a T-helper cytokine that regulates humoral immunity and cell-mediated anti-tumor responses," Immunology, 112: 177-182, 2004.
Sivakumar, "Interleukin-21 elicits durable T and NK cytotoxicity: basic biology to clinical trials," J /mmunother., 27(6):S56, 2004.
Strengell et al., "IL-21 up-regulates the expression of genes associated with innate immunity and Thl response," J / mmunol., 169(7):3600-3605, 2002.
Tollerud et al., "The influence of age, race, and gender on peripheral blood mononuclear-cell subsets in healthy nonsmokers," J Clin. /mmunol., 9(3):214-222, 1989.
Vari and Hart, "Loading DCs with Ag," Cytotherapy, 6(2):111-121, 2004.
Baron et al., Immunity, vol. 18, 193-204, Feb. 2003 (Year: 2003).
Beckhove et al. (J. Clin. Invest. 114:67-76 (2004)). (Year: 2004).
Meidenbauer et al. (J. Immunol. 2003;170;2161-2169).
Mortarini et al. (Cancer Research, 2003, 63, 2535-2545).
Champagne et al., Nature (Land.), 410: 106-111, 2001.
Rufer et al., Blood. 2003;102:1779-1787.
"Of Mice and Not Men: Differences between Mouse and Human Immunology"; Mestas, et al.; J Immunol 2004; 172:2731-2738; http://www.jimmunol.org/content/172/5/2731.
"IL-21 Influences the Frequency, Phenotype, and Affinity of the Antigen-Specific CDS T Cell Response"; Li, et al.; J Immunol 2005; 175:2261-2269; http://www.jimmunol.org/content/175/4/2261.
"IL-21 Limits NK Cell Responses and Promotes Antigen-Specific T Cell Activation: A Mediator of the Transition from Innate to Adaptive Immunity"; Kasaian, et al.; Immunity, vol. 16, 559-569, Apr. 2002; Cell Press.
"Elucidating the elite: mechanisms of control in HIV-1 infection"; O'Connell, et al.; Dept. of Medicine, Johns Hopkins School of Medicine; 2009 Elsevier Ltd.
"Transferred melanoma-specific CDS+ T cells persist, mediate tumor regression, and acquire central memory phenotype"; Chapuis et al., Proc Natl Acad Sci U SA. 109(12):4592-4597 (Epub Mar. 5, 2012).
"Transition of late-stage effector T cells to CD27+ CD28+ tumor-reactive effector memory T cells in humans after adoptive cell transfer therapy"; Powell, et al.; Blood. Jan. 1, 2005; 105(1 ):241-50; Epub, Sep. 2, 2004.
Zhu et al., "The narrow-spectrum HDAC inhibitor entinostat enhances NKG2D expression without NK cell toxicity, leading to enhanced recognition of cancer cells," Pharm Res., (2015), vol. 32, No. 3: 779-792.
Zheng et al., "HDAC inhibitors enhance T cell chemokine expression and augment response to PD-1 immunotherapy in lung adenocarcinoma," Clin Cancer Res., (2016), vol. 22, No. 16: 4119-4132.
Nolte et al., "Generation of Melanoma-Specific Cytotoxic T Lymphocytes for Allogeneic Immunotherapy," Journal of Immunotherapy, (2003), vol. 26, No. 3: 257-269.
Yee et al., "Methos for Use of Peptide-MHC Tetramers in Tumor Immunology," Methods in Molecular Medicine, (2001), vol. 61: 353-362.
Loschinski et al, "IL-21 modulates memory and exhaustion phenotype of T-cells in a fatty acid oxidation-dependent manner," Oncotarget, (2018), vol. 9, No. 17: 13125-13138.
McCaw et al., "Modulation of antitumor immunity with histone deacetylase inhibitors," Immunotherapy, (2017), vol. 9, No. 16: 1359-1372.
Zhang et al., "Epigenetic Manipulation Restores Functions of Defective CD8+ T Cells From Chronic Viral Infection," Molecular Therapy, (2014), vol. 22, No. 9: 1698-1706.
Wang et al, "Histone Deacetylase Inhibitors and IL21 Cooperate to Reprogram Human Effector CD8þ T Cells to Memory T Cells," Cancer Immunol Res, (2020), vol. 8, No. 6: 794-805.

* cited by examiner

Figure 3
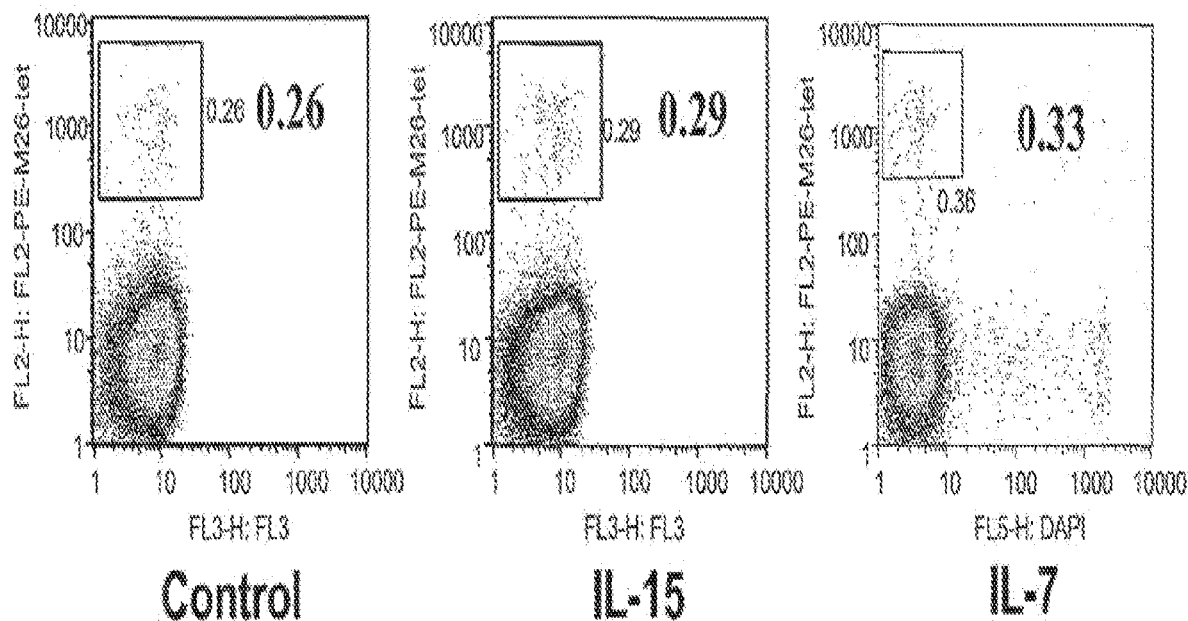
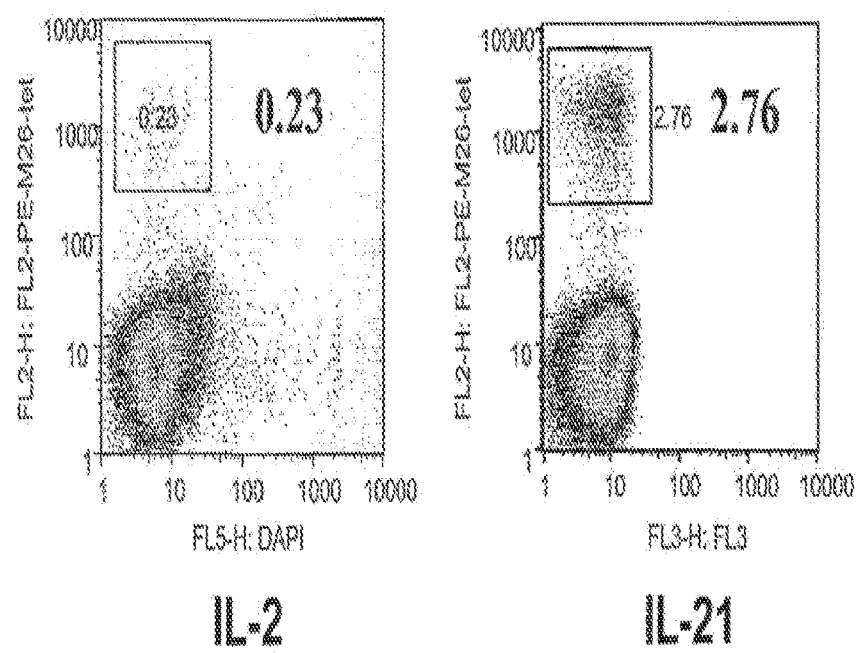

Figure 8
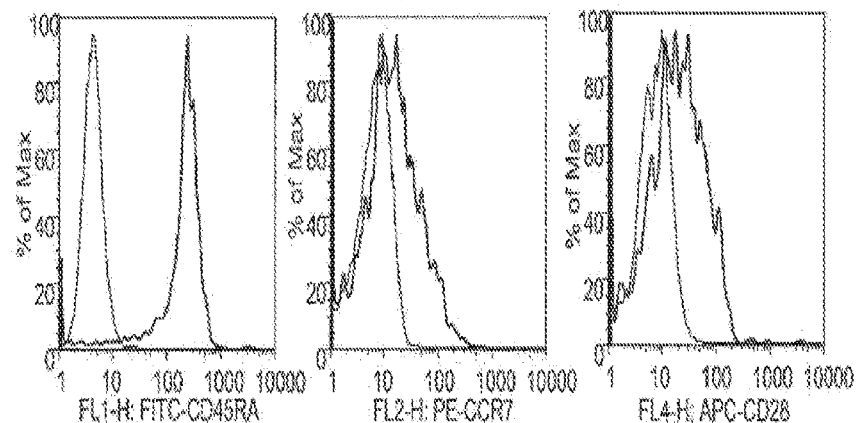
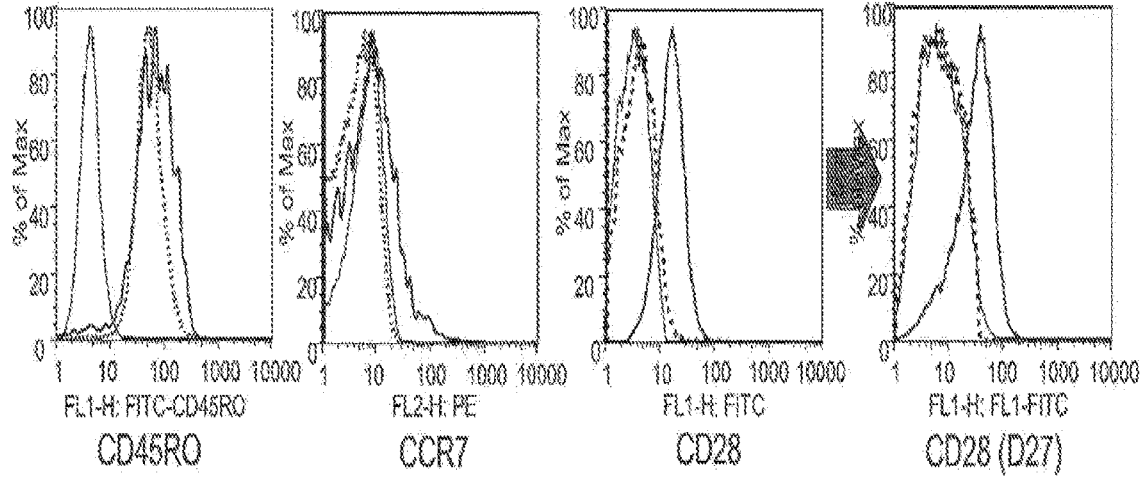

Combination of IL-21 to IL-6/12 leads to enhanced frequency and prolonged survival of antigen-specific CTL

SEQUENCE LISTING

<160> NUMBER OF SEQ ID NOS: 2

<210> SEQ ID NO 1
<211> LENGTH: 642
<212> TYPE: DNA
<213> ORGANISM: Homo sapiens

<400> SEQUENCE: 1

| | | |
|---|---|---|
| gctgaagtga aaacgagacc aaggtctagc tctactgttg gtacttatga gatccagtcc | 60 |
| tggcaacatg gagaggattg tcatctgtct gatggtcatc ttcttgggga cactggtcca | 120 |
| caaatcaagc tcccaaggtc aagatcgcca catgattaga atgcgtcaac ttatagatat | 180 |
| tgttgatcag ctgaaaaatt atgtgaatga cttggtccct gaatttctgc cagctccaga | 240 |
| agatgtagag acaaactgtg agtggtcagc ttttcctgt tttcagaagg cccaactaaa | 300 |
| gtcagcaaat acaggaaaca atgaaaggat aatcaatgta tcaattaaaa agctgaagag | 360 |
| gaaaccacct tccacaaatg cagggagaag acagaaacac agactaacat gcccttcatg | 420 |
| tgattcttat gagaaaaaac cacccaaaga attcctagaa agattcaaat cacttctcca | 480 |
| aaagatgatt catcagcatc tgtcctctag aacacacgga agtgaagatt cctgaggatc | 540 |
| taacttgcag ttggacacta tgttacatac tctaatatag tagtgaaagt catttctttg | 600 |
| tattccaagt ggaggagccc tattaaatta tataaagaaa ta | 642 |

<210> SEQ ID NO 2
<211> LENGTH: 162
<212> TYPE: PRT
<213> ORGANISM: Homo sapiens

<400> SEQUENCE: 2

Met Arg Ser Ser Pro Gly Asn Met Glu Arg Ile Val Ile Cys Leu Met
1               5                   10                  15

Val Ile Phe Leu Gly Thr Leu Val His Lys Ser Ser Ser Gln Gly Gln
            20                  25                  30

Asp Arg His Met Ile Arg Met Arg Gln Leu Ile Asp Ile Val Asp Gln
        35                  40                  45

Leu Lys Asn Tyr Val Asn Asp Leu Val Pro Glu Phe Leu Pro Ala Pro
    50                  55                  60

Glu Asp Val Glu Thr Asn Cys Glu Trp Ser Ala Phe Ser Cys Phe Gln
65                  70                  75                  80

Lys Ala Gln Leu Lys Ser Ala Asn Thr Gly Asn Asn Glu Arg Ile Ile
                85                  90                  95

Asn Val Ser Ile Lys Lys Leu Lys Arg Lys Pro Pro Ser Thr Asn Ala
            100                 105                 110

Gly Arg Arg Gln Lys His Arg Leu Thr Cys Pro Ser Cys Asp Ser Tyr
        115                 120                 125

Glu Lys Lys Pro Pro Lys Glu Phe Leu Glu Arg Phe Lys Ser Leu Leu
    130                 135                 140

Gln Lys Met Ile His Gln His Leu Ser Ser Arg Thr His Gly Ser Glu
145                 150                 155                 160

Asp Ser

METHODS OF USING IL-21 FOR ADOPTIVE IMMUNOTHERAPY AND IDENTIFICATION OF TUMOR ANTIGENS

CROSS REFERENCE TO RELATED APPLICATIONS

This application is a continuation of U.S. patent application Ser. No. 14/468,326, filed Aug. 25, 2014, which is a continuation of U.S. patent application Ser. No. 12/617,018, filed Nov. 12, 2009, which is a continuation of U.S. patent application Ser. No. 11/285,970, filed Nov. 23, 2005, which claims the benefit of U.S. Provisional Application Ser. No. 60/630,727, filed Nov. 24, 2004, each of which is herein incorporated by reference.

BACKGROUND OF THE INVENTION

Cytokines generally stimulate proliferation or differentiation of cells of the hematopoietic lineage or participate in the immune and inflammatory response mechanisms of the body. The interleukins are a family of cytokines that mediate immunological responses. Central to an immune response is the T cell, which produces many cytokines and plays a role in adaptive immunity to antigens. Cytokines produced by the T cell have been classified as type 1 and type 2 (Kelso, A. *Immun. Cell Biol.*, 76:300-317, 1998), Type 1 cytokines include IL-2, IFN-γ, LT-α, and are involved in inflammatory responses, viral immunity, intracellular parasite immunity and allograft rejection. Type 2 cytokines include IL-4, IL-5, IL-6, IL-10 and IL-13, and are involved in humaral responses, helminth immunity and allergic response. Shared cytokines between Type 1 and 2 include IL-3, GM-CSF and TNF-α. There is some evidence to suggest that Type 1 and Type 2 producing T cell populations preferentially migrate into different types of inflamed tissue.

IL-21 has been shown to be a potent modulator of cytotoxic T cells and NK cells. (Parrish-Novak, et al., *Nature* 408:57-63, 2000; Parrish-Novak, et al., *J. Leuk. Bio.* 72:856-863, 2002: Collins et al., *Immunol. Res.* 28:131-140, 2003; Brady, et al. *J. Immunol.* 172:2048-58, 2004.) T cell responses include enhancement of primary antigen response as modulation of memory T cell functions.

In murine studies, IL-21 potentiates the maturation and effector function of NK cells and promotes T cell activation in response to alloantigen (Kasaian et al., *Immunity* 16:559-569, 2002). As a cytokine which limits NK cell expansion and promotes activation of murine CD8 T cells, IL-21 is believed to play a role in the transition from innate to adaptive immunity (Kasaian, supra, 2002). Among CD4 T cells, IL-21 has been described as both a Th1 (T helper 1) cytokine which upregulates the expression of genes associated with innate immunity (Strengell et al., *J. Immunol.* 170:5464, 2003) as well as a Th2 cytokine that inhibits the differentiation of naïve Th cells into IFN-gamma-producing Th1 cells (Wurster et al., *J. Exp. Med.* 196:969, 2002). The effects of IL-21 in the development of innate immunity and CD4 Th responses are well-characterized (Strengell supra, 2003; Strengell et al., *J. Leukoc. Biol.* 76:416, 2004), but its role in the antigen-specific CD8+ T cell response, particularly in humans, had not been fully explored. The present invention provides methods for inducing a high affinity antigen-specific cytotoxic T cell response by administering IL-21. Induction of a high affinity CD8 response against self antigens, which are represented increasingly as potential immune targets in cancer immunotherapy demonstrate a significant role for IL-21 in antigen-specific anti-tumor strategies. Thus, the present invention provides methods for administering IL-21 as an adjuvant in tumor vaccines and ex vivo expansion of tumor antigen-specific cytotoxic T cells for use in adoptive immunotherapy. The present invention also provides methods for administering IL-21 as an adjuvant for vaccines and ex vivo expansion of antigen-specific cytotoxic T cells in general against viruses, and other target antigens. These and other uses should be apparent to those skilled in the art from the teachings herein.

SUMMARY OF THE INVENTION

In one aspect, the present invention provides a method for identifying a tumor antigen comprising co-culturing tumor material isolated from a subject with peripheral blood mononuclear cells (PBMCs) in the presence of an IL-21 composition and antigen presenting cells (APCs), isolating a T cell population from the culture, enriching for individual T cells from the T cell populating, and characterizing the T cell clones for antigen specificity. In certain embodiments, enrichment is cloning of individual T cells.

In another aspect of the present invention a method of identifying a tumor antigen is provided which comprises co-culturing tumor material from a subject with an isolated T cell population that is non-terminally differentiated in the presence of an IL-21 composition; cloning individual T cells from the T cell population; and characterizing T cell clones for antigen-specificity. In one embodiment, the isolated T cell population does not include CD4+ cells.

In certain embodiments of these methods, the PBMCs or T cell population is an autologous cell population. In other embodiments, the tumor material comprises total RNA, lysed tumor cells, necrotic tumor cells, tumor proteins or apoptotic bodies. In another embodiment, co-culturing is in the presence of the IL-21 composition and one or more additional cytokines.

In another aspect, the present invention provides method of preparing a T cell population for use in adoptive immunotherapy comprising identifying PBMCs having a histocompatible phenotype to a subject having a tumor; co-culturing tumor material or tumor associated peptides from the patient with the peripheral blood mononuclear cells (PBMCs) in the presence of an IL-21 composition and APCs; expanding these cells in culture; and and reintroducing these cells back into the patient. In one embodiment, the PBMCs are autologous. In one embodiment, the T cell population is autologous. In another embodiment, the tumor material comprises total RNA, lysed tumor cells or apoptotic bodies. In another embodiment, the PBMCs or T cells are allogenic.

In another aspect, the present invention provides a method of preparing a T cell population for use in adoptive immunotherapy comprising identifying T cell population having a histocompatible phenotype to a subject having a tumor; co-culturing tumor material from the subject with the T cell population in the presence of an IL-21 composition and APCs; expanding these cells in culture; and and reintroducing these cells back into the subject. In one embodiment, T cell population is naïve or non-terminally differentiated. In another embodiment, the T cell population is autologous. In another embodiment, the tumor material comprises total RNA, lysed tumor cells or apoptotic bodies.

BRIEF DESCRIPTION OF THE FIGURES

FIG. 1. On day 7 after stimulation, $10^6$ Cells from each experiment group were harvested and stained with 20 μg/ml of peptide/MHC tetramer (PE, vertical axis) and a vital dye (PI or DAPI, horizontal axis). Data are expressed as percentage of tetramer positive cells among gated lymphocytes (purified CD8+ cells).

FIG. 2. The absolute number in millions of tetramer+ cells corresponding to untreated and IL-21 treated cultures from donors CG, NE and LD depicted in A., and the fold increase in absolute numbers of IL-21 treated to untreated cultures. C. Cultures from a normal healthy donor, CG, and a patient with metastatic melanoma, ST, were analyzed on Day 7 after the first (Stim 1) and second (Stim 2) stimulation in the presence or absence of IL-21 during Stim 1. IL-2 and IL-7 were added following Stim 2. Data are expressed as percentage of tetramer positive cells among gated lymphocytes (purified CD8+ cells). Results above are representative of three separate experiments for each donor.

FIG. 3 illustrates that exposure to other gamma-chain cytokines, IL-2, IL-7 or IL-15 does not enhance generation of antigen-specific CTL. CD8+ cells from a healthy HLA-2+ donor were stimulated in vitro with autologous mature dendritic cells pulsed with the MART-1, M26 peptide as described the Examples. On day 7 after stimulation, $10^6$ Cells from each experiment group were harvested and stained with 20 μg/ml of peptide/MHC tetramer (PE, vertical axis) and a vital dye (PI or DAPI, horizontal axis). Data are expressed as percentage of tetramer positive cells among gated lymphocytes (purified CD8+ cells). Data are representative of cultures from 3 HLA-A2+ donors.

FIG. 8 illustrates IL-21 treated cultures yield a population of $CD28^{hi}$ antigen-specific CTL. Cells were collected from pre-stimulation PBMC, and then 7 days following stimulation with MART-1 peptide-pulsed autologous dendritic cells in the absence or presence of IL-21. Cells were stained for MART-1-Tetramer and simultaneously with either CD45RA or CD45 RO, CD28 and CCR7 (FIG. 7). Histogram analysis for individual phenotypic markers was performed on gated MART-1-tetramer staining cells, CD28 expression on gated tetramer-staining cells is also shown for culture from Day 27 after stimulation. These results are representative of cultures from 3 donors.

DESCRIPTION OF THE INVENTION

Figure 1:
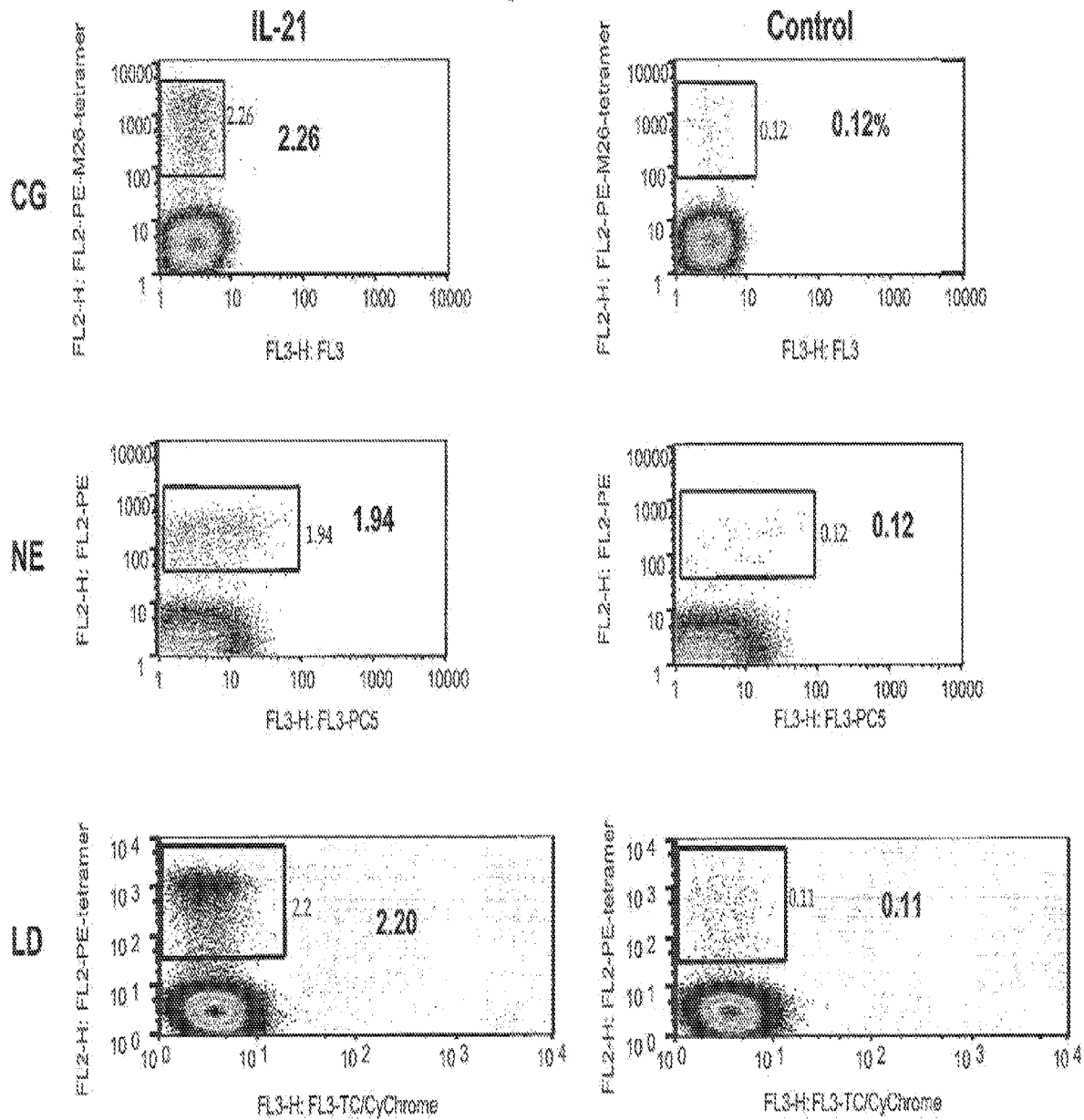
FIGS. 1 and 2 illustrate that IL-21 enhances the generation of MART-1 specific CTL., CD8+ T cells from healthy HLA-A2+ donors CG, NE and LD were stimulated in vitro with autologous mature dendritic cells pulsed with the MART-1, M26 peptide as described in the Examples.

Prior to setting forth the invention in detail, it may be helpful to the understanding thereof to define the following terms:

The term "allelic variant" is used herein to denote any of two or more alternative forms of a gene occupying the same chromosomal locus. Allelic variation arises naturally through mutation, and may result in phenotypic polymorphism within populations. Gene mutations can be silent (no change in the encoded polypeptide) or may encode polypeptides having altered amino acid sequence. The term allelic variant is also used herein to denote a protein encoded by an allelic variant of a gene.

The terms "amino-terminal" and "carboxyl-terminal" are used herein to denote positions within polypeptides. Where the contest allows, these terms are used with reference to a particular sequence or portion of a polypeptide to denote proximity or relative position. For example, a certain sequence positioned carboxyl-terminal to a reference sequence within a polypeptide is located proximal to the carboxyl terminus of the reference sequence, but is not necessarily at the carboxyl terminus of the complete polypeptide.

The term "cancer" or "cancer cell" is used herein to denote a tissue or cell found in a neoplasm which possesses characteristics which differentiate it from normal tissue or tissue cells. Among such characteristics include but are not limited to: degree of anaplasia, irregularity in shape, indistinctness of cell outline, nuclear size, changes in structure of nucleus or cytoplasm, other phenotypic changes, presence of cellular proteins indicative of a cancerous or pre-cancerous state, increased number of mitoses, and ability to metastasize. Words pertaining to "cancer" include carcinoma, sarcoma, tumor, epithelioma, leukemia, lymphoma, polyp, and scirrus, transformation, neoplasm, and the like.

The term "co-administration" is used herein to denote that an IL-21 polypeptide or protein and a second therapeutic molecule may be given concurrently or at a different times. The co-administration may be a single co-administration of both IL-21 and the second therapeutic molecule or multiple cycles of co-administration. Co-administration need not be the only times either IL-21 or the second therapeutic molecule is administered to a patient.

The term "combination therapy" is used herein to denote that a subject is administered at least one therapeutically effective dose of IL-21 and a second therapeutic molecule. The IL-21 may be a mature polypeptide, fragment thereof, fusion or conjugate that demonstrates IL-21 biological activity.

The term "enhance" when in reference to an immune response is used herein to mean increasing the scale and/or efficiency of an immune response or extending the duration of the immune response. The term is used interchangeably with "augument." An immune response includes, but is not limited to, enhanced cytolytic activity, apoptotic activity or increases in CD8+ T cell numbers or survival.

The term "isolated", when applied to a polynucleotide, denotes that the polynucleotide has been removed from its natural genetic milieu and is thus free of other extraneous or unwanted coding sequences, and is in a form suitable for use within genetically engineered protein production systems. Such isolated molecules are those that are separated from their natural environment and include cDNA and genomic clones. Isolated DNA molecules of the present invention are free of other genes with which they are ordinarily associated, but may include naturally occurring 5' and 3' untranslated regions such as promoters and terminators. The identification of associated regions will be evident to one of ordinary skill in the art (see for example, Dynan and Tijan, *Nature* 316:774-78, 1985).

An "isolated" polypeptide or protein is a polypeptide or protein that is found in a condition other than its native environment, such as apart from blood and animal tissue. In a preferred form, the isolated polypeptide is substantially free of other polypeptides, particularly other polypeptides of animal origin. It is preferred to provide the polypeptides in a highly purified form, i.e. greater than 95% pure, more preferably greater than 99% pure. When used in this context, the term "isolated" does not exclude the presence of the same polypeptide in alternative physical forms, such as dimers or alternatively glycosylated or derivatized forms.

The term "level" when referring to immune cells, such as NK cells, T cells, in particular cytotoxic T cells, B cells and the like, refers to the number of cells or the activity of cells. An increased level is either increased number of cells or enhanced activity of cell function.

The term "level" when referring to viral infections refers to a change in the level of viral infection and includes, but is not limited to, a change in the level of CTLs or NK cells (as described above), a decrease in viral load, an increase antiviral antibody titer, decrease in serological levels of alanine aminotransferase, or improvement as determined by histological examination of a target tissue or organ. Determination of whether these changes in level are significant differences or changes is well within the skill of one in the art.

The term "neoplastic", when referring to cells, indicates cells undergoing new and abnormal proliferation, particularly in a tissue where in the proliferation is uncontrolled and progressive, resulting in a neoplasm. The neoplastic cells can be either malignant, i.e. invasive and metastatic, or benign.

A "polynucleotide" is a single- or double-stranded polymer of deoxyribonucleotide or ribonucleotide bases read from the 5' to the 3' end. Polynucleotides include RNA and DNA, and may be isolated from natural sources, synthesized in vitro, or prepared from a combination of natural and synthetic molecules. Sizes of polynucleotides are expressed as base pairs (abbreviated "bp"), nucleotides "nt"), or kilobases ("kb"). Where the context allows, the latter two terms may describe polynucleotides that are single-stranded or double-stranded. When the term is applied to double-stranded molecules it is used to denote overall length and will be understood to be equivalent to the term "base pairs". It will be recognized by those skilled in the art that the two strands of a double-stranded polynucleotide may differ slightly in length and that the ends thereof may be staggered as a result of enzymatic cleavage; thus all nucleotides within a double-stranded polynucleotide molecule may not be paired.

A "polypeptide" is a polymer of amino acid residues joined by peptide bonds, whether produced naturally or synthetically. Polypeptides of less than about 10 amino acid residues are commonly referred to as "peptides".

A "protein" is a macromolecule comprising one or more polypeptide chains. A protein may also comprise non-peptidic components, such as carbohydrate groups. Carbohydrates and other non-peptidic substituents may be added to a protein by the cell in which the protein is produced, and will vary with the type of cell. Proteins are defined herein in terms of their amino acid backbone structures; substituents such as carbohydrate groups are generally not specified, but may be present nonetheless.

The term "receptor" denotes a cell-associated protein that binds to a bioactive molecule (i.e., a ligand) and mediates the effect of the ligand on the cell. Membrane-bound receptors are characterized by a multi-peptide structure comprising an extracellular ligand-binding domain and an intracellular effector domain that is typically involved in signal transduction. Binding of ligand to receptor results in a conformational change in the receptor that causes an interaction between the effector domain and other molecule(s) in the cell. This interaction in turn leads to an alteration in the metabolism of the cell. Metabolic events that are linked to receptor-ligand interactions include gene transcription, phosphorylation, dephosphorylation, increases in cyclic AMP production, mobilization of cellular calcium, mobilization of membrane lipids, cell adhesion, hydrolysis of inositol lipids and hydrolysis of phospholipids. In general, receptors can be membrane bound, cytosolic or nuclear; monomeric (e.g., thyroid stimulating hormone receptor, beta-adrenergic receptor) or multimeric (e.g., PDGF receptor, growth hormone receptor, IL-3 receptor, GM-CSF receptor, G-CSF receptor, erythropoietin receptor and IL-6 receptor).

Molecular weights and lengths of polymers determined by imprecise analytical methods (e.g., gel electrophoresis) will be understood to be approximate values. When such a value is expressed as "about" X or "approximately" X, the stated value of X will be understood to be accurate to ±10%.

All references used are herein incorporated by reference.

The present inventions are directed to use of IL-21 to increase proliferation and survival of antigen-specific T cells, IL-21 enhancement of antigen-specific T cells will be useful for increasing the frequency of antigen-specific T cells, enriching for populations of antigen-specific T cells with enhanced affinity, and generating a population of antigen-specific T cells with increased CD28 expression and "helper-independent" phenotype (Widmer et al., Nature 294: 750, 1981; Topp et al., J. Exp Med 198(6):947, 2003: Cheng et al., J Immunol 169:4990, 2002)

In certain aspects the present invention provides methods that comprise culturing naïve T cells in the presence of an IL-21 composition and an antigen resulting in a cytotoxic T cell population that has a higher affinity for an antigen than T cells cultured in the absence of IL-21. Of particular interest are tumor antigens. High affinity antigen-specific T cells have the capacity to recognize and kill tumor, whereas a low affinity T cell may have tumor antigen-specificity, yet still not recognize and kill a tumor cell. Affinity of a T cell for a tumor is in part dependent on the antigen density that is presented by the tumor cell. If antigen presentation on the tumor cell is low, then is more likely that only high affinity T cells will be able recognize the tumor cell and initiate cytolysis. Moreover, the methods of the present invention can be used to increase T cell frequency to levels that are high enough for expansion and adoptive cell transfer without further antigen-specific T cell enrichment and thereby greatly decrease the time to therapy and obviate the requirement for further selection or cloning.

In another aspect of the present invention, the methods of the present invention comprise generating an antigen-specific CTL population that has a high affinity for self antigens by culturing T cells that have non-terminally differentiated to an IL-21 composition. In one embodiment, the T cells are isolated naïve T cells. Once the antigen-specific T cells population has been expanded ex vivo, the cells are reintroduced into the patient. In certain embodiments, IL-21 administration to the patient will continue and may be in combination with other therapies.

In another aspect, the methods of the present invention provide methods for enhancing the repetoire of antigens recognized by a T cell population. The methods comprise co-culturing tumor material such as a tumor cell line or derivative thereof (e.g. total RNA, lysed tumor cells, apoptotic bodies) with autologous T cells isolated from a subject. The tumor material and the T cells are cultured in the presence of an IL-21 composition, and after allowing T cells to proliferate, the T cells are cloned. Antigen-specific T cells are identified and further analyzed to characterize the antigen-specificity.

A. Description of IL-21

Human IL-21 (SEQ ID NO:1 and SEQ ID NO:2) was originally designated zalpha11 Ligand, and is described in commonly-owned U.S. Pat. Nos. 6,307,024, and 6,686,178, which are incorporated herein by reference. The IL-21 receptor is described in U.S. Pat. No. 6,057,128. The IL-21 receptor, previously designated zalpha11 (SEQ ID NO:5 and SEQ ID NO:6), and heterodimeric receptor IL-21R/IL-2Rγ are also described in commonly-owned U.S. Pat. Nos. 6,576,744, 6,803,451, 6,692,924 and WO 00/17235, which are incorporated herein by reference. As described in these publications, IL-21 was isolated from a cDNA library generated from activated human peripheral blood cells (hPBCs), which were selected for CD3. CD3 is a cell surface marker unique to cells of lymphoid origin, particularly T cells.

The amino acid sequence for the IL-21R indicated that the encoded receptor belonged to the Class I cytokine receptor subfamily that includes, but is not limited to, the receptors for IL-2, IL-4, IL-7, IL-15, EPO, TPO, GM-CSF and G-CSF (for a review see, Cosman, "The Hematopoietin Receptor Superfamily" in *Cytokine* 5(2): 95-106, 1993). The IL-21 receptor has been identified on NK cells, T cells and B cell indicating -21 acts on hematopoietic lineage cells, in particular lymphoid progenitor cells and lymphoid cells. Other known four-helical-bundle cytokines that act on lymphoid cells include IL-2, IL-4, IL-7, and IL-15. For a review of four-helical-bundle cytokines, see, Nicola et al., *Advances in Protein Chemistry* 52:1-65, 1999 and Kelso, A., *Immunol. Cell Biol.* 76:300-317, 1998.

For IL-21, a secretory signal sequence is comprised of amino acid residues 1 (Met) to 29 (Seri), and a mature polypeptide is comprised of amino acid residues 30 (Gln) to 162 (Ser) (as shown in SEQ ID NO: 2). The corresponding polynucleotide sequence is shown in SEQ ID NO:1. Those skilled in the art will recognize that the sequence disclosed in SEQ ID NO:1 represents a single allele of human IL-21 and that allelic variation and alternative splicing are expected to occur.

B. Use of IL-21 Vaccine Therapy, Adoptive Immunotherapy and Identification of Tumor Specific Antigens The present invention is based in part on a study of both human healthy donors and melanoma patients where a positive regulatory role for IL- 21 in the induction of a primary antigen-specific human CD8+ T cell response was demonstrated. Using peptide-MHC tetramers to track a rare but measurable naïve T cell population recognizing a normal self antigen, in the presence of IL-21, the frequency and absolute numbers of antigen-specific CD8+T cells that could be elicited increased by more than 20-fold compared to cultures grown in the absence of IL-21. The enhanced generation of an antigen-specific T cell response is specific to this gamma-chain receptor cytokine since the addition of IL-2, IL-7 or IL-15 during initial printing had no added effect over cultures that received no cytokine. IL-21-exposed and antigen-primed T cells retained the capacity to respond to growth-promoting cytokines, such as IL-2 and IL-7, and could be readily isolated and expanded. The present invention provides IL-21 enhanced generation of human antigen-specific CD8+ T cells characterized by CD28 upregulation and expression of high affinity TCR resulting in antigen-driven helper-independent IL-2 production, increased target avidity, and augmented antigen-specific tumor killing. The present invention provides methods of using IL-21 for induction of a human antigen-specific CD8+ T cell responses and immunotherapy, particularly adoptive cell therapy.

In the studies described herein, the IL-21 augmented antigen-specific response was limited to the naïve and not memory T cell population using pre-selected responder T cells, Naïve T cells have not previously seen antigen and have the potential to recognize and bind a single, unique antigen. A tumor antigen is a peptide or polypeptide or peptide complex that has a different expression profile from antigen found on a non-tumor cells. For example, a non-tumor antigen may be expressed in higher frequency or density by tumor cells than by non-tumor cells. A tumor antigen may differ from a non-tumor antigen structurally, for example, the antigen could be expressed as a truncated polypeptide, have some mutation in the amino acid sequence or polynucleotide sequence encoding the antigen, be misfolded, or improperly modified post-translationally. Similarity to antigens that are present on normal, non-tumor cells in the host organism allow the tumor cells to escape the host's immunological surveillance mechanisms.

Observation that tumor-associated antigens generated specific immunological responses which attacked tumors provided researchers a basis to develop tumor specific antigen cancer therapies. However, tumors express a multitude of antigens, many of which have not been isolated or characterized. Moreover, not all tumor antigens are expressed at levels high enough to stimulate a sufficient immune response.

In recent years, many genes encoding tumor antigens that can be recognized by cytotoxic T lymphocytes have been identified from cDNA of human tumor cells (Gomi et al., *J. Immunol.* 163:4994-5004, 1999.) Examples include the genes HER/neu (Peoples et al., *Proc. Natl Acad. Sci. USA,* 92:432-436, 1995) and mutant CASP-8 (Mandruzzato et al., *J. Exp. Med.,* 186:785-793. 1997). Tumor antigen-specific T cells can be isolated from patients, however maintaining these T cell cultures has been difficult. Tumor antigen-specific T cells can be localized in blood, lymphoid tissue such as the spleen, or can be from the tumor itself. Generally, tumor tissue is biopsied and a cell suspension is cultured in vitro. It has been shown that antigen-specific tumor cells in the presence of cytokine, such as IL-2, IL-7, IL-4, and IL-15 survive longer (Vella et al., *PNAS* 95:3810-3815, 1998). In the instant invention, addition of IL-21 to cultures of tumor antigen-specific T cells in the presence of primary antigen presentation by dendritic cells resulted in a significant increase in the absolute numbers of antigen-specific T cells beyond that seen with IL-15, IL-6, IL-12, 2 or IL-7 alone. Thus, the present invention provides methods for identifying new tumor specific antigens and enhancing tumor antigen-specific T cell populations to target those tumors by exposing T cells to IL-21. The methods for enhancing the repetoire of antigens recognized by a T cell population by generating tumor-specific cell lines arose from having demonstrated that IL-21 compositions enhance proliferation of antigen-specific T cell populations when antigen is presented to non-terminally differentiated T cells. The methods comprise co-culturing tumor material such as a tumor cell line or derivative thereof (e.g. total RNA, lysed tumor cells, apoptotic bodies) with autologous T cells isolated from a subject. The tumor material and the T cells are cultured in the presence of an IL-21 composition, and after allowing T cells to proliferate, the T cells are enriched, for example the T cells can be cloned. In some embodiments, the need for IL-2 or other growth factors is minimized by administration of IL-21. In other embodiments, it is not necessary to have CD4+ T cells present in the culture. Antigen-specific T cells are identified are further analyzed to characterize the antigen-specificity. (See, van der Bruggen *Science* 254:1643, 1991 and Engelhard et al., *Mol. Immunol.* 39:127, 2002).

It is known that a larger number of MART-1 specific T cells reside among the naïve population (Pittet et al, *J. Exp. Med.* 190:705, 1999) however, measurable frequencies of MART-1-specific T cells can also be detected among the memory population (D'Souza et al., *Int. J. Cancer* 78:699, 2004), and yet these failed to expand when IL-21 was added. In the case of patients with melanoma, prior encounter with antigen-bearing tumor cells may lead to defective signalling among memory T cells rendering them unresponsive to IL-21 mediated proliferation in vitro (Zippelius, et al, *Cancer Res.* 64:2865, 2004; Lee et al., *Nature Medicine* 5:677, 1999).

Antigen-primed T cells undergo increased proliferation and decreased apoptosis when exposed to IL-21 compared to their untreated counterparts, hence providing methods for enhancing T cell-mediated vaccines and providing an adjuvant for immunotherapeutic cancer treatments. IL-21 treatment led to upregulated CD28 expression and enriched for a population of T cells expressing a stable unique phenotype, CD45RO+, CD28hi, CCR7-CD8+. This phenotype may be characterized as intermediate between a naïve (CD45RO−, CD28+, CCR7+) and memory (C45RO+, CD28−, CCR7−/+) T cell (Tomiyama, et al., *J. Exp. Med.* 198:947, 2003), CD28+CD8+ T cells represent potentially more effective CTL for adoptive immunotherapy since they can provide an antigen-driven autocrine signal for proliferation. Such helper-independent CD8 T cells would not require exogenous help in the form of IL-2 or CD4+ T cells to survive and expand (Ho et al., *Cancer Cell* 3:431, 2003; and Topp et al., *J. Exp. Med.* 198:947, 2003). Thus, the present invention provides methods for treating an immune-mediated disease by providing a subject with a CD8+ T cell population that has enhanced cytotoxic activity in the absence or reduced presence of additional cytokines, such as IL-2, or CD4+ T cells. The methods are particularly useful for ex vivo expansion of cytolytic, antigen-specific CD8+ T cells, but may also be used in vivo when additional cytokines result in unwanted side effects or CD4+ cell populations are compromised.

The examples disclosed herein demonstrate that exposure to IL-21 during primary in vitro stimulation also led to the generation of antigen-specific T cell clones of uniformly higher affinity and target cell avidity. These clones were represented by diverse TCR Vbetas suggesting that this was not likely the result of an expanded population of a few high affinity clones, but a more global effect on the T cell repertoire. Previous studies have shown an increased probability of isolating higher affinity T cell clones when cytokines such as IL-10, that downregulate the stimulatory capacity of APCs, are used in culture (Tsai et al., *Critical Rev. Immunol.* 18:65, 1998). IL-21 (Brandt et al., *Blood* 102:4090, 2003) has been shown to lead to maturational arrest among murine DC resulting in reduced MHC expression and decreased stimulatory capacity for T cell activation. However, in that case, IL-21 was added to human DCs that had already undergone full maturation. In preliminary studies, the addition of IL-21 to mature DC did not affect surface expression of MHC-Class I, HLA-DR, CD80, CD83 or CD86 compared to untreated DC. While not intending to be bound by theory, the results suggest dampened expression of surface stimulatory molecules is not likely an explanation for the enhanced generation of high affinity T cells in vitro. Pre-incubation of mature human DC with IL-21 also had no effect on the frequency or affinity of CD8+tetramer+ T cells that could be generated.

The use of IL-21 in augmenting an antigen-specific CD8 T cell response has been explored in mouse models and found to be highly effective in eradicating aggressive tumors (Ma et al., *J. Immunol.* 171:608, 2002; Kishida et al., *Mol. Ther.* 8:552, 2003; Moroz et al., *J. Immunol.* 173:900, 2003). The selective effect of IL-21 on naïve vs memory T cells suggests a greater influence during priming, and in fact, murine studies demonstrate a strong priming effect characterized by a slow rejection response and induction of prolonged antitumor memory. IL-21 promotes longterm survival of previously activated antigen-specific CD8 T cells in vivo as a result of reduced apoptosis through an indeterminate mechanism possibly involving STAT3 phosphorylation or induction of a central memory phenotype (Brenne et al., *Blood* 99:3756, 2002). Some of these effects may be attributable to CD28 upregulation among IL-21-treated CD8 T cells.

Methods of using T cell populations for adoptive cell therapy in treatment of human subjects are known to clinicians skilled in the art. T cell populations prepared according to the methods described herein and known in the art can be used in such methods. For example, adoptive cell therapy using tumor-infiltrating lymphocytes, with MART-1 antigen specific T cells have been tested in the clinic (Powell et al., *Blood* 105:241-250, 2005). Patients with renal cell carcinoma have been vaccinated with irradiated autologous tumor cells. Harvested cells were secondarily activated with anti-CD3 monoclonal antibody and IL-2, then readministered to the patients (Chang et al., *J. Clinical Oncology* 21:884-890, 2003.)

The present invention provides methods for enhancing adoptive immunotherapy by providing a patient with a level of enhanced immunity by stimulating cells ex vivo, and then readministering them to the patient. The cells are histocompatible with the subject, and may be allogenic or autologous. The method of preparing comprises isolating peripheral blood mononuclear cells (PBMCs) from a patient, expanding these cells in culture to very high numbers in a culture media comprising an IL-21 composition, and then to reintroducing these cells back into patients. The growth of these effector cells, which include NK cells, LAK cells, and tumor-specific T-cells, may require additional cytokines such as IL-2 (Dudley et al., *J. Immunother.* 24:363-73, 2001) or IL-15 (Marks-Konczalik et al., *Proc Natl Acad Sci USA*, 97:11445-50 2000; Waldmann T A, *Nat Med.*, 9:269-77, 2003; Fehniger et al., *Cytokine Growth Factor Rev.*, 13:169-83, 2002.) Following the transfer of cells back into patients, methods are employed to maintain their viability by treating patients with cytokines that could include IL-21 and IL-2 (Bear et al., *Cancer Immunol. Immunother.* 50:269-74, 2001; and Schultze et al., *Br. J. Haematol.* 113:455-60, 2001). In another embodiment, once PBMCs are isolated, the cells can be further isolated to provide a more homogeneous culture of CD8+ cells, and these cells are cultured in the presence of an IL -21 composition and then readministered to the patient. Because IL-21 can increase T cell frequency to levels that are high enough for expansion and adoptive transfer without further antigen-specific T cell enrichment, the present invention provides methods that can greatly decrease the time to therapy and obviate the requirement for further selection and/or cloning.

The present invention provides a method of preparing a T cell population for use in adaptive immunotherapy comprising identifying PBMCs having a histocompatible phenotype to a tumor patient; co-culturing tumor material from the patient with the peripheral blood mononuclear cells (PBMCs) in the presence of an IL-21 composition and antigen presenting cells (APCs), such as autologous dendritic cells, monocytes, B cells, EBV-transformed B cell lines, allogeneic EBV transformed B cell lines expressing the shared restricting allele, artificial antigen presenting cells (Yee et al., *Proc Natl Acad Sci.* 99(25):16168, 2002; Oelke et al., *Nat Med.* 9(5):619-24, 2003; Maus et al., *Clin Immunol.* 106(1):16-22, 2003: Cai et al., *Immunol Rev.* 165:249-65, 1998); expanding these cells in culture; and reintroducing these cells back into the patient. In one embodiment, the PBMCs are autologous. In another embodiment, the tumor material comprises peptide, total RNA, lysed tumor cells or apoptotic bodies.

The present invention also provides a method of preparing a T cell population for use in adoptive immunotherapy comprising identifying a T cell population having a histocompatible phenotype to a tumor patient; co-culturing tumor material from the patient with the T cell population in the presence of an IL-21 composition and APCs; expanding these cells in culture: and and reintroducing these cells back into the patient. In one embodiment, the T cell population is autologous (Dudley et al., *Science* 290:850, 2002).

The present invention provides a method of preparing a T cell population for use in adoptive immunotherapy comprising T cells, bone marrow cells or PBMCs (including NK cells) engineered (by viral transduction, transfection, electroporation or other methods of introducing genetic material) to express a T cell receptor or a chimeric T cell receptor fused with signaling molecules, that recognize the target antigen: culturing in the presence of an IL-21 composition; expanding these cells in culture; and and reintroducing these cells back into the patient. (Hughes et al., *Hum Gene Ther* 16(4):457, 2005; Roszkowski et al., *Cancer Res* 65(4):1570, 2005; Cooper et al., *Blood* 101:1637, 2003; Alajez et al., *Blood* 105:4583, 2005). In one embodiment, the T cell population is autologous.

The present invention also provides methods for improving cancer vaccine therapy. Many tumors express foreign antigens that can potentially serve as targets for destruction by the immune system (Boon. T., *Adv. Cancer Res.* 58:177-211, 1992). Cancer vaccines generate a systemic tumor-specific immune response in a subject that comprises both humoral and cellular components. The response is elicited from the subject's own immune system by administering a vaccine composition at a site distant from the tumor or at the site of a localized tumor. The antibodies or immune cells bind the tumor antigen and lyse the tumor cells. However, there remains a need for increased proliferation of T cell populations capable of produced enhanced immune responses in vivo.

Numerous methods for immunizing patients with cancer antigens have been employed, and a variety of techniques are being used to amplify the strength of the immune response following antigen delivery (reviewed in Rosenberg, S A. (Ed.), Principles and practice of the Biologic Therapy of Cancer., 3rd edition, Lippincott Williams & Wilkins, Philadelphia, Pa., 2000). Methods in which L-21 can be used in combination with a tumor vaccine include, but are not limited to, the delivery of autologous and allogeneic tumor cells that either express the IL-21 gene or in which IL-21 is delivered in the context of a adjuvant protein. Similarly, IL-21 can be delivered in combination with injection of purified tumor antigen protein, tumor antigen expressed from injected DNA, or tumor antigen peptides that are presented to effector cells using dendritic cell-based therapies. Examples of these types of therapies include the use of cytokines like IL-2 in the context of vaccination with modified tumor cells (Antonia et al., *J. Urol.* 167:1995-2000, 2002; and Schrayer et al., *Clin. Exp. Metastasis* 19:43-53, 2002). DNA (Niethammer et al., *Cancer Res.* 61:6178-84, 2001), and dendritic cells (Shimizu et al., *Proc. Nat. Acad. Sci USA* 96:2268-73, 1999). IL-21 can be used as an anti-cancer vaccine adjuvant.

The determination of vaccine efficacy is difficult to evaluate. The ultimate demonstration of efficacy is the rate of tumor regression, duration of disease-free survival, or, at least, time-to progression (TTP), these end-points require following patient progress for years. To provide a more immediate means for evaluating efficacy there is an ongoing search for so called "surrogate markers" that would permit early measurements and be predictive of clinical outcome. As of today, in vitro measurements of tumor- and/or vaccine-specific immune responses have not proven successful as surrogate markers (see, Srivastava P., *Nat Immunol.* 1:363-366, 2000).

For any cancer therapy each protocol may define tumor response assessments differently, but exemplary guidelines can be found in Clinical Research Associates Manual, Southwest Oncology Group, CRAB, Seattle, Wash., Oct. 6, 1998, updated August 1999. According to the CRA Manual (see, chapter 7 "Response Assessment"), tumor response means a reduction or elimination of all measurable lesions or metastases. Disease is generally considered measurable if it comprises bidimensionally measurable lesions with clearly defined margins by medical photograph or X-ray, computerized axial tomography (CT), magnetic resonance imaging (MRI), or palpation. Evaluable disease means the disease comprises unidimensionally measurable lesions, masses with margins not clearly defined, lesion with both diameters less than 0.5 cm, lesions on scan with either diameter smaller than the distance between cuts, palpable lesions with diameter less than 2 cm, or bone disease. Non-evaluable disease includes pleural effusions, ascites, and disease documented by indirect evidence. Previously radiated lesions which have not progressed are also generally considered non-evaluable.

Positive therapeutic outcome can be measured using objective status protocols to assess solid tumor response. Representative criteria include the following: (1) Complete Response (CR) defined as complete disappearance of all measurable and evaluable disease with no new lesions, and no disease related symptoms. No evidence of non-evaluable disease; (2) Partial Response (PR) defined as greater than or equal to 30% decrease from baseline in the sum of products of perpendicular diameters of all measurable lesions, with no progression of evaluable disease, no new lesions. According the RESIST criteria, patients with at least one measurable lesion; (3) Progression defined as 20% or an increase of 10 $cm^2$ in the sum of products of measurable lesions over the smallest sum observed using same techniques as baseline, or clear worsening of any evaluable disease, or reappearance of any lesion which had disappeared, or appearance of any new lesion, or failure to return for evaluation due to death or deteriorating condition (unless unrelated to this cancer); (4) Stable or No Response defined as not qualifying for CR, PR, or Progression, (See, *Clinical Research Associates Manual, supra.*)

The invention is further illustrated by the following non-limiting examples.

EXAMPLES

Example 1

A. Cell Lines and Reagents

Melanoma cell lines A375 (CRL 1619; American Type Culture Collection (ATCC), Manassas, Va.), and Mel 526 (Arrighi et al., *Cancer Res.* 60(16):4446-52, 2000; Marcinola et al, *J. Immunother Emphasis Tumor Immunol.* 19(3): 192-205, 1996,) were maintained in RPMI with HEPES (25 mM), L-glutamine (4 mM), penicillin (50 U/ml), streptomycin (50 mg/ml), sodium pyruvate (10 mM), non-essential amino acids (1 mM), and 10% fetal bovine serum (Hyclone, Utah), Both lines express the HLA-A2 allele, but only Mel 526 expresses the MART-1 antigen. The T2 cell line is a TAP-deficient T-B-cell hybrid expressing the HLA-A2 allele. EBV-LCL cell lines are Epstein-Barr virus transformed lymphoblastoid cell lines (Yee, FHCRC, Seattle, Wash.).

B. Induction of Human Antigen-Specific CD8+ T Cells

Melanoma M26-35 peptide specific T cells were generated (Yee et al., *PNAS* 99:16168, 2002; Yee et al., *J. Immunol.* 162:2227, 1999; Tsai et al., *J. Immunol.* 158:1796, 1997). Donor blood was typed by the HLA Typing Lab at the Puget Sound Blood Center (Seattle, Wash.). CD8+ T cells were first isolated by a CD8 positive isolation kit (Dynabead, Dynal, Oslo, Norway) from leukapheresis PBMCs, suspended in CTL medium consisting of RPMI 1640, 25 mM HEPES, 2 mM L-glutamine, penicillin (50 U/ml), streptomycin (50 mg/ml) (Life Technologies, Gaithersburg, Md.), and 10% human serum from normal donors, and then placed in 6 well tissue culture dishes (Costar, Corning Incorporated, Coring, N.Y.) at $6 \times 10^6$ cell/well. Mature DCs were harvested and pulsed with 40 µg/ml of synthesized peptides at $2 \times 10^6$ cell/ml in the presence of 3 µg/ml of β2 microglobulin (Scripps Lab, San Diego, Calif.) in PBS with 1% human serum albumin (Lite Technologies, Gaithersburg, Md.) for 4 hrs at room temperature. After washing three times with sterile PBS (Life Technologies), DCs were mixed with purified CD8 T cells at $3 \times 10^5$ cells/well in 6 well plate. Cytokines, IL-15 (10 ng/ml, R&D Systems, Minneapolis, Minn.), IL-2 (10 U/ml, Chiron, Emeryville, Calif.), IL-7 (10 ng/ml, R&D Systems), or IL-21 (30 ng/ml, ZymoGenetics, Seattle, Wash.) were added individually to each well immediately after the culture initiated. IL-2 (50 IU/ml) and IL-7 (10 ng/ml) were added one day after 2nd stimulation to further facilitated expansion of activated antigen-specific T cells.

DC were generated (Bender et al., *J. Immunol. Methods* 196:121, 1996) by exposing adherent PBMC to IL-4 (500 U/ml, R&D) and GM-CSF (800 U/ml, Amgen, Thousand Oaks, Calif.) in AIM·V® medium (Life Technologies) followed by maturation using IL-1β at 2 ng/ml, IL-6 at 1000 U/ml, TNF-α at 10 ng/ml (R&D Systems) and PGE-2 at 1 µg/ml (Sigma-Aldrich, St. Louis, Mo.) for an additional 2 days. The mature DC population contained more than 90% CD83+ DCs on day 8 as determined by FACS analysis.

C. Antibody Plus Peptide-MHC Tetramer Staining of T Cells

PE or APC labeled M26-MHC-Tetramer and G154-MHC-tetramers were produced in the immune monitoring lab at Fred Hutchinson Cancer Center based on previously described protocols (Altman et at., *Science* 274:94, 1996). For sample analysis, $0.5 \times 10^6$ cells in 25 µl of 2% FCS/PBS were first stained with peptide tetramer-PE or APC (final concentration of 20 µg MHC/ml) for one hour at room temperature, followed by anti-CD28-APC (BD, PharMingen, San Diego, Calif.) or anti-CD28-FITC (Caltac Lab, Burlingame, Calif.), anti-CCR7-PE and anti-CD45RO or anti-CD45RA-FITC (BD, PharMingen, San Diego, Calif.) staining for 20 min at 4° C. After washing with PBS, cells were resuspended in PBS containing 2% FBS and DAPI was added. Data were acquired using a FACScalibur flow cytometer and CellQuest (BD) and analyzed using FlowJo software (Tree Star, San Carlos, Calif.).

D. Enrichment for Naïve and Memory Subsets

T cells were purified from human peripheral blood mononuclear cells by the sequential application of a combination of magnetic beads and an Automacs magnetic sorter (Miltenyi Biotech, Auburn Calif.). CD8+ cells were isolated using negative selection with the CD8 isolation kit II. Subsequent naïve (CD8+CD45RO−CD45RA+CD62L+) cell selection involved depletion of memory CD8 cells using a CD45RO bead, followed by positive selection of CD62L positive cells by staining with PE-conjugated CD62L antibody (BD Phamingen, San Diego, Calif.) and incubation with an antiPE bead. Memory cell isolation (CD8+CD45RA−CD45RO+) involved depletion of the naïve population with a CD45RA+ bead. Typical purities assessed by FACs were in excess of 95%.

E. Cloning and Expansion of Ag-Specific CTL

The cloning and expansion procedures as described Yee, supra, 2002; Riddell et al., *J. Immunolog, Methods* 128:189, 1990, were used to isolate T cells. Tetramer+ sorted T cells were plated at limiting dilution in 96-well round-bottomed plates (Nalge Nune International, Denmark) in the presence of irradiated feeder cells (PBL and LCL) at a responder to stimulator ratio of 1:50,000 together with anti-CD3 mAb (OKT3, Ortho Tech, Raritan, N.J.) and 50 UL-2/ml in 0.2 ml of CTL medium. Wells, positive for clonal growth were identified 10-14 days after plating and screened in a microcytotoxicity assay. Peptide-specific clones were transferred to 25-cm2 flasks (Costar, Corning Incorporated, Coring, N.Y.), restimulated with anti-CD3 mAb, and irradiated allogeneic PBL and LCL were added as feeder cells for rapid expansion. The cultures were fed with IL-2 at 50 U/ml 24 hrs after restimulation and then every 3 days. After 14 days, cells were used for further analyses or cryopreserved.

F. In Vitro Cytotoxicity Assay

Target cells (375, 526 melanoma cell lines or T2 cells) were labeled with 100 µCi $^{51}$Cr and co-cultured with effector cells for 4 hrs at 37° C. plus 5% $CO_2$. For peptide dose titration studies, T2 were pulsed with a peptides at concentrations ranging from $10^8$ to $10^2$ pg/ml for 1 hour and then washed prior to $^{51}$Cr labeling. Released $^{51}$Cr was measured with a gamma scintillation counter and percent specific lysis was determined by using the formula: percent specific release=Experimental release−Spontaneous release/Total release. Spontaneous release was <10% of the total release in all assays.

G. MHC/Peptide Dissociation Assay to Identify High and Low Affinity CTL Clones

CTL clones were stained with APC-Tetramer (20 µg/ml) for 1 h at room temperature and washed once with cold PBS to eliminate unbound tetramer. Cells were incubated in the presence of an excess (100 µg/ml) of PE-labeled tetramer to prevent rebinding of APC-Tetramer after their dissociation from TCR. During this period, aliquots of cells were collected at different time points and fixed in 1% paraformaldehyde for flow cytometry analysis. The rate of APC tetramer dissociation is inversely correlated with TCR affinity (Dutoit et al., *J. Immunol.* 168:1167, 2002).

Example 2

IL-21 Augments the Frequency of Antigen-Specific CD8 T Cells Generated Following Primary In Vitro Stimulation A. model system for primary in vitro stimulation of antigen-specific T cells was established by isolating CD8+ T cells from PBMC of HLA A2+ healthy donors and co-culturing with autologous mature dendritic cells pulsed with immunogenic epitopes of the tumor-associated self antigen, MART-1 (M26-35 peptide). Cultures were grown with no added cytokine or with IL-21 (FIG. 1). The frequency of MART-1-specific CD8 T cell responses in cultures was evaluated 7 days after stimulation by tetramer staining. In representative healthy donors (CG, NE and LD), a 16 to 20-fold increase in MART-1 specific CD8+ T cell frequency was observed in IL-21 exposed cultures compared with no cytokine control cultures (0.12 vs 2.26%; 0.12 vs 1.95 and 0.11 vs 2.2% respectively) following one cycle of in vitro stimulation (FIG. 1). The absolute numbers of antigen-specific T cells generated in IL-21-treated cultures exceeded control cultures by more than 20 to 30-fold (Table 1).

TABLE 1

|  | CG | NE | LD |
| --- | --- | --- | --- |
| Control | $0.22 \times 10^6$ | $0.30 \times 10^6$ | $0.43 \times 10^6$ |
| IL-21 | $7.80 \times 10^6$ | $8.15 \times 10^6$ | $14.1 \times 10^6$ |
| Fold Increase | 35 | 27 | 33 |

The use of other cytokines belonging to the common gamma-chain cytokine receptor family, IL-2, IL-7 and IL-15 during primary in vitro stimulation produced no added effect on the frequency of MART-1-specific CD8+ T cells compared to no cytokine control cultures (FIG. 3).

The addition of IL-2 and IL-7, however, does promote the ex vivo expansion of previously primed, antigen-experienced T cells as demonstrated by our group and others (Gervois, et al., *Clin Cancer Res* 6:1459-1467, 2000; Liao et al., *Mol Ther* 9:757-764, 2004). When added to cultures following a second in vitro stimulation, IL-2 (10 U/ml) and IL-7 (10 ng/ml) produced a further increase in the magnitude of the MART-1 specific CD8 T cell population among IL-21 treated (11.8%) over untreated cultures (2.43%) (FIG. 2, donor CG).

These studies demonstrate that IL-21 has the capacity to augment tumor-associated antigen-specific CTL responses in patients with melanoma, a tumor which shares expression of MART-1. In a representative patient, the frequency of MART-1-specific CTL generated in IL-21 treated compared with untreated cultures after two cycles of in vitro stimulation demonstrate a 40-fold increase when IL-21 was added compared to untreated controls (19.1 vs 0.46%) (FIG. 2, patient ST).

Figure 4:
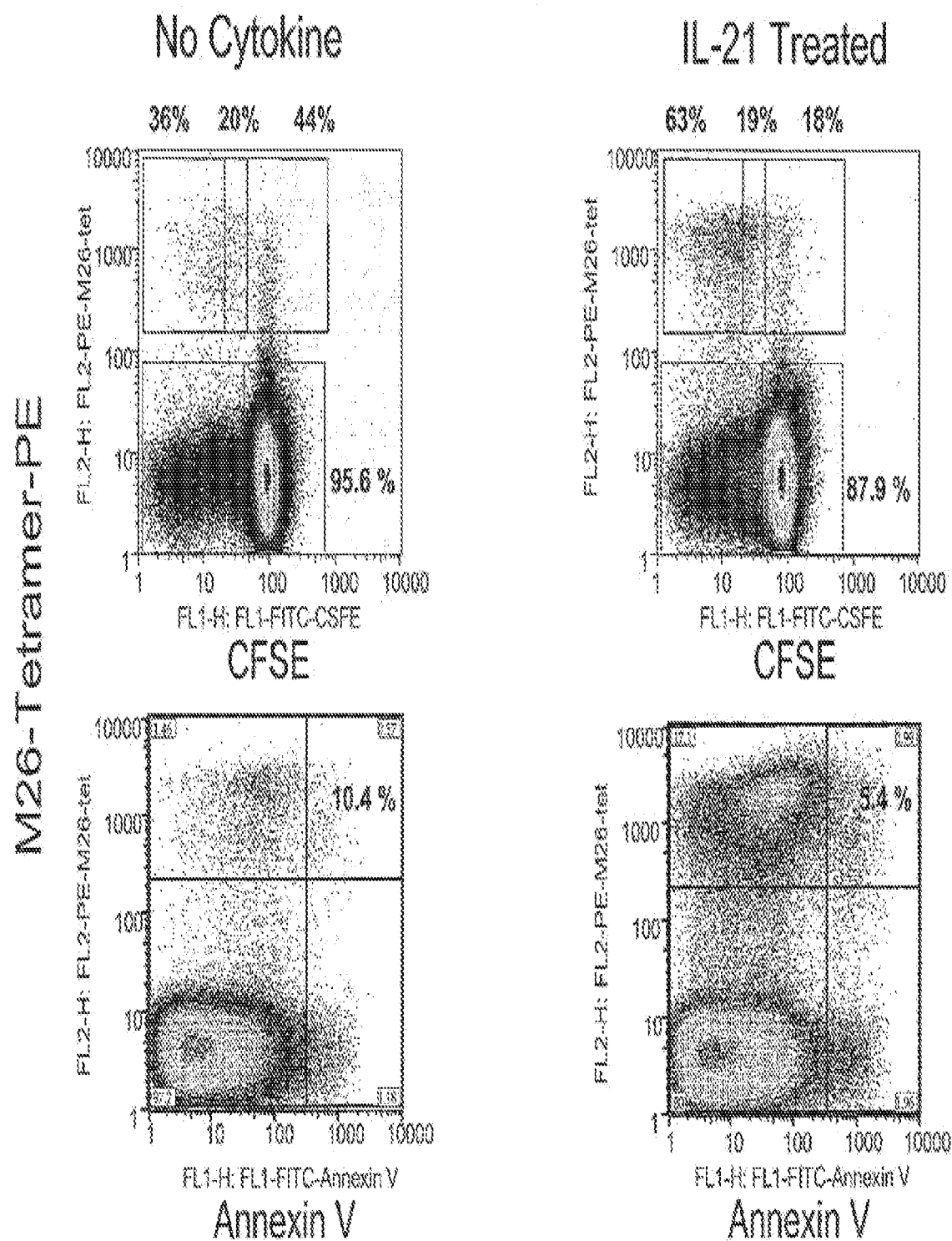
FIG. 4 illustrates IL-21 treated cells undergo increased proliferation and decreased apoptosis during primary in vitro stimulation. Purified populations of naïve (CD45RA+, CD62L+) lymphocytes were pre-incubated with CFSE and stimulated with MART-1 peptide in the absence (No Cytokine) or presence of IL-21 (IL-21-treated). On Day 7, cells were stained with MART-1 peptide-MHC Tetramer-PE and analyzed for the fraction of dividing cells (CFSE) or cells undergoing apoptosis (Annexin V), CFSE-stained cells lose fluorescence intensity with successive divisions. Results are expressed as percentage of non-dividing (rightmost box), dividing (center) and rapidly dividing (leftmost) tetramer+ cells. For apoptotic cells, Annexin V staining tetramer+ cells are represented as a percentage in the right upper quadrant.

To evaluate if the increase in frequency and absolute numbers of antigen-specific CD8 T cells generated among IL-21 treated cultures was due to enhanced proliferation and/or enhanced survival, naïve CD8 T cells were labelled with CFSE, stimulated in vitro with MART-1 peptide pulsed autologous DC and at Day 7, evaluated for fraction of dividing cells (as determined by quantum decreases in CFSE staining accompanying each cell division) and apoptosis (Annexin V staining). For CFSE staining, analyses performed on the tetramer-positive (MART-1-specific) T cell population demonstrate a substantially greater fraction of non-dividing cells (rightmost compartment) among untreated cultures (44%) than IL-21 treated cultures (18%) (FIG. 4), In fact, the ratio of rapidly dividing (leftmost compartment) to nondividing antigen-specific T cells is more than 3 fold greater among the IL-21 treated compared to the untreated cultures (63:18% vs. 36:44%). That the effect of IL-21 on T cell proliferation is antigen-specific is demonstrated by the large fraction of tetramer-negative (non-antigen-specific) T cells remaining in the non-dividing phase (95.6 and 87.9%).

Figure 2:
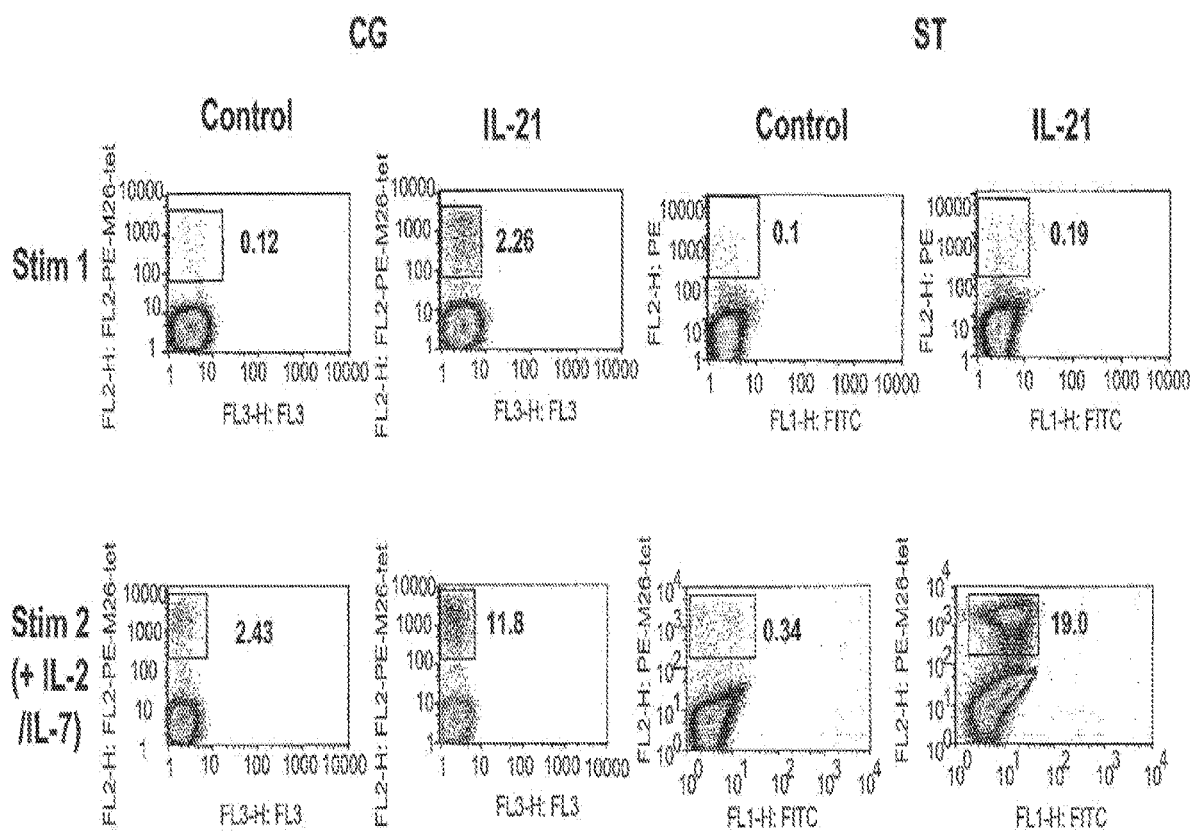

Annexin V staining of tetramer-positive T cells on Day 7 reveals a modest decrease in the fraction of apoptotic (Annexin V+) antigen-specific T cells among IL-21 treated cultures compared to untreated cultures (10.4 vs 5.4% of tetramer+ T cells, respectively, FIG. 2). Taken together, these results suggest that the increase in frequency and absolute numbers of antigen-specific CD8 T cells generated among IL-21 treated cultures was due predominantly to enhanced antigen-specific cellular proliferation and in minor part to increased survival or decreased apoptosis.

Example 3

Figure 5:
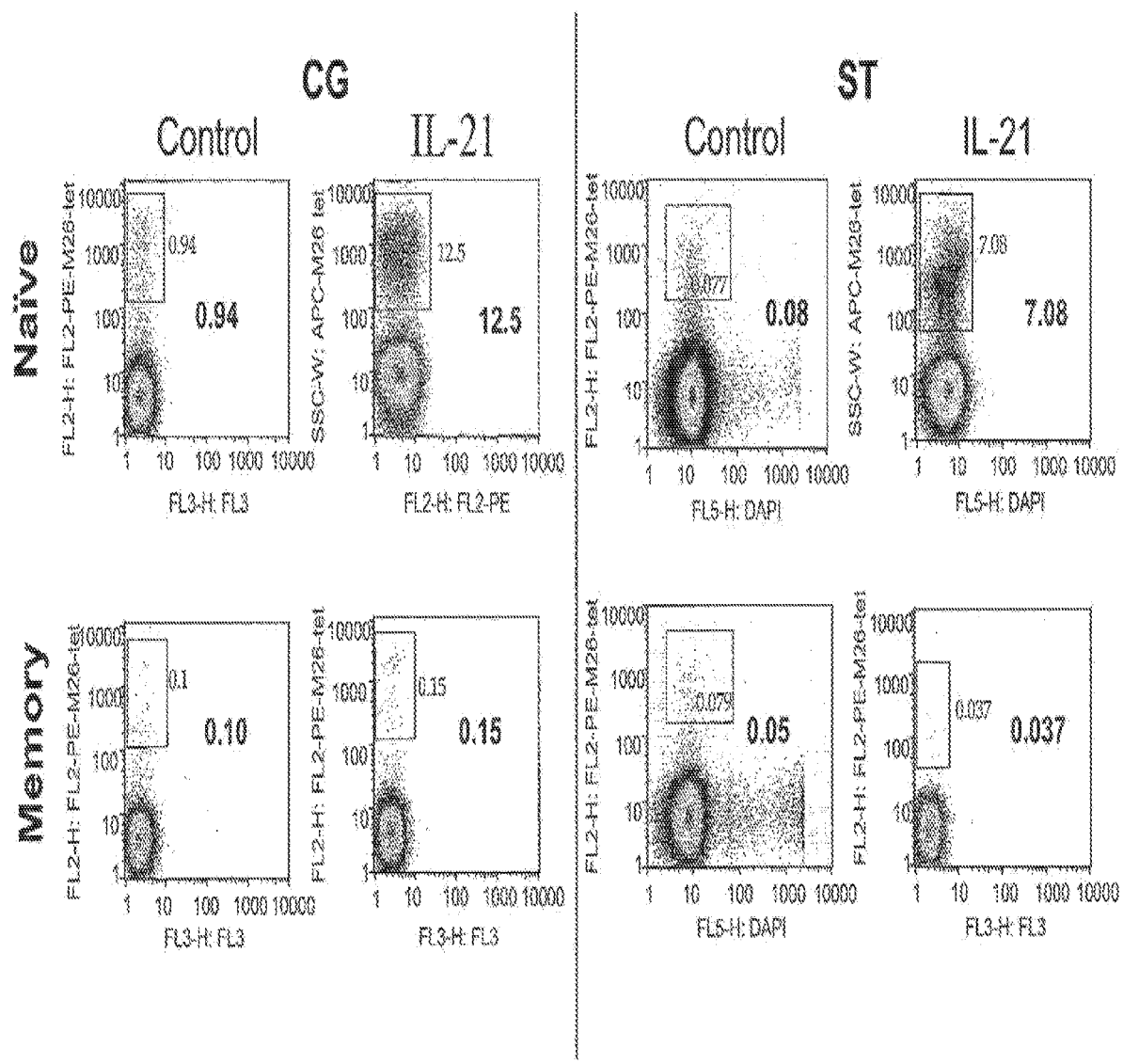
FIG. 5 illustrates IL-21 influences primarily naïve vs. memory CD8+ T cells. Highly purified populations of naïve (CD45RA-+, CD62L+) or memory (CD45RO+) T cells from a healthy normal donor (CG) and a donor with melanoma (ST) were evaluated for induction of antigen-specific responses to MART-1 peptide in the absence or presence of IL-21. The percentage of MART-1-specific CTL are expressed as percentage tetramer+ cells among total gated lymphocytes (CD8+ purified cells) after two cycles of in vitro stimulation. Results are representative of experiments performed on 2 other normal healthy donors (NE, LD) and 2 other patient donors (AM, RE).

IL-21 Enhances Antigen-Specific T Cell Response Among a Predominantly Naïve CTL Population The capacity of IL-21 to enhance the generation of antigen-specific CD8+ T cells was evaluated separately among naïve and memory T cells. Purified populations of naïve (>98% CD45RA+, CD62L+) CD8+ T cells were compared with memory (100% CD45RO+) CD8+ T cells from both a healthy normal donor (CG) (FIG. 5) and an individual with metaplastic melanoma (ST). Whereas IL-21 exerts minimal effect on the frequency of MART-1 specific cells generated from memory CD8+ T cells (0.10 to 0.15% and 0.05 to 0.037%, a 12 to 90-fold increase is observed among naïve CD8 T cells following IL-21 exposure (0.94 to 12.5% and 0.08 to 7.08%) providing evidence that IL-21 influences primarily naïve T cells.

Example 4

Figure 6:
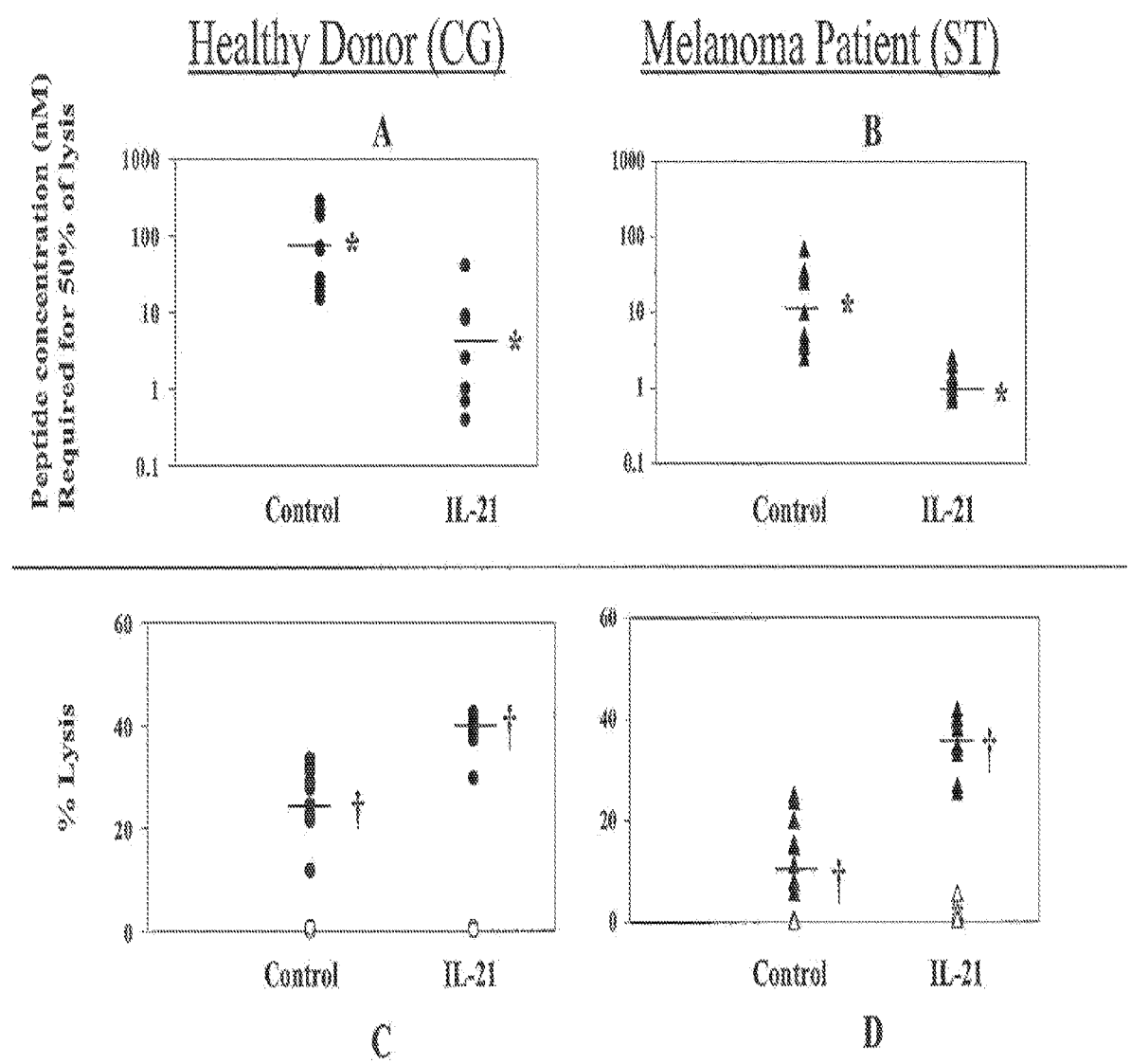
FIG. 6 illustrates IL-21 preferentially induces the generation of high avidity antigen specific CTL. Individual MART-1 specific CD8+ T cell clones were isolated from cultures stimulated in the absence (Control) or presence (IL-21) of IL-21. 8-12 representative CTL clones from each experimental condition were evaluated for target affinity in a chromium release assay using T2 cells pulsed with decreasing concentrations of M26 peptide (peptide dose titration analysis). Data are expressed as the concentration (nM) required to reach 50% maximal lysis of target cells. On average, CTL clones generated by IL-21, demonstrated a decreased peptide dose requirement for specific lysis compared to CTL clones generated in no cytokine control (* p<0.01). A: healthy donor, CG (●); B: melanoma patient, ST (Δ). These same clones were evaluated for specific reactivity to a MART-1+ tumor cell line (526) at E/T ratio of 10 to 1 in a standard 4 hr $^{51}$Chromium release assay (CRA). Significantly greater lysis of antigen-positive tumor (526 ●, ▲) with background lysis of antigen-negative tumor (375 ○, Δ) was observed in CTL clones isolated from IL-21 treated culture than those isolated from no cytokine control († p<0.01). C: healthy donor, CG (●, ○); D: melanoma patient, ST (Δ, ▲). Results are representative of 3 normal healthy donors and 3 patient donors.

CTL Generated From IL-21-Treated Cultures Represent a Population of High Affinity Antigen-Specific T Cells with Enhanced Tumor Reactivity To further characterize the function of antigen-specific T cell populations generated under the influence of IL-21 at the clonal level, tretramer+CD8+ T cells from both a healthy donor (CG) and melanoma patient (ST) were sorted on day 7 and cloned at limiting dilution into 96-well plates. MART-1 specific clones identified by microcytotoxicity assays were expanded and tested for 1) the peptide concentration required for 50% maximal lysis ($P_{50}$) of peptide pulsed T2 cells and 2), the ability to lyse antigen-positive melanoma targets. For evaluating $P_{50}$, the HLA-A2-transfected EBV B cell line, T2, was titrated with peptide concentrations ranging from $10^7$ to $10^2$ pM. Results are presented as the peptide dose requirement (nM) for 50% lysis ($P_{50}$). CTL clones generated from IL-21 treated cultures required a >one log lower peptide dose requirement than their untreated counterparts—mean 3 nM (range 0.6-30 nM) vs. mean 80 nM (range 16-500 nM), respectively (FIG. 6A). A similar effect of IL-21 was seen for CTL clones generated from melanoma patient (ST) (FIG. 6B).

At an effector to target (E:T) ratio of 10:1, T cell clones isolated following stimulation in the presence of IL-21 displayed much higher specific lytic activity against the MART-1 positive 526 melanoma cell line (35-45%) than those isolated in the absence of IL-21 (FIGS. 6C and 6D). For each individual clone, increased tumor reactivity was coincident with decreased peptide dose requirement suggesting that CTL generated in the presence of IL-21 exhibited a higher avidity interaction with its cognate target.

Figure 7:
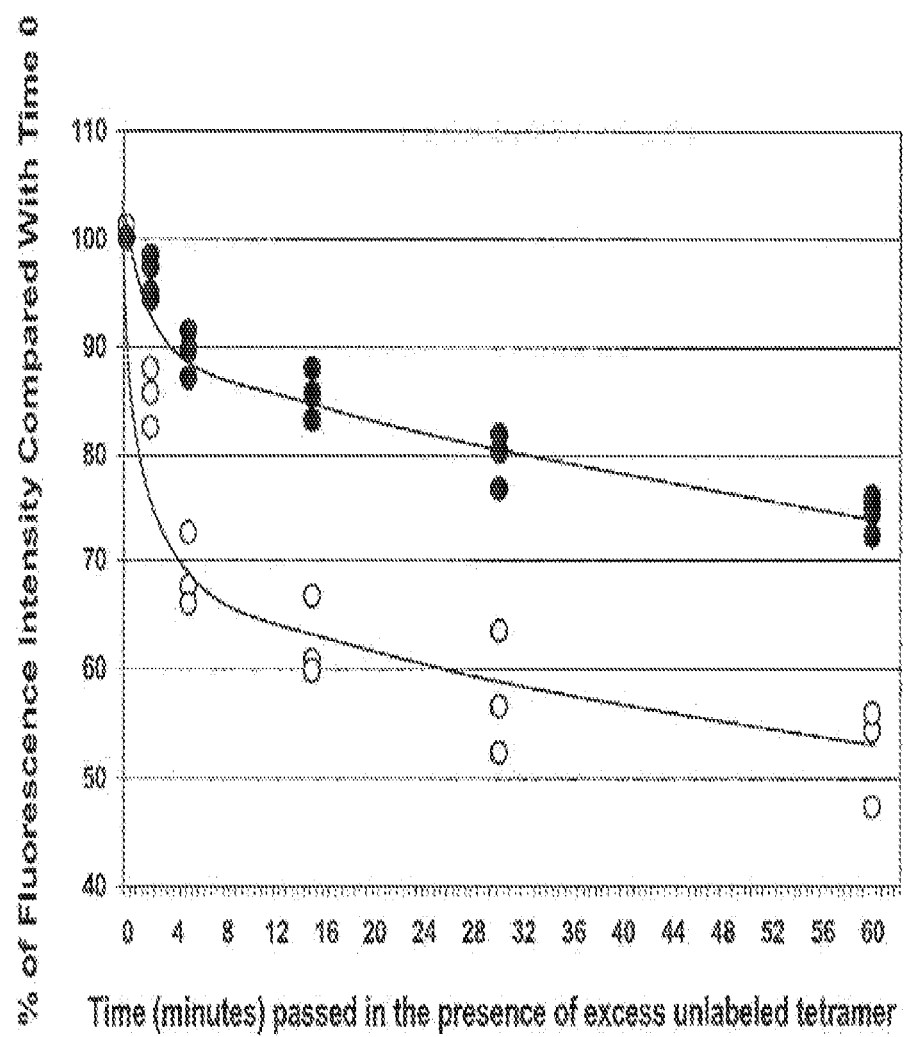
FIG. 7 illustrates IL-21 treated cultures enrich for CTL expressing higher affinity TCR:tetramer dissociation assay. The tetramer dissociation assay, which depicts the fraction of bound tetramer remaining over time in the presence of an excess of unlabeled tetramer, was used as a surrogate measure of the TCR dissociation rate or TCR affinity of individual clones. The fraction of PE-tetramer labelled MART-1-specific CTL clones from IL-21 treated cultures (●) was compared with clones from untreated cultures (○) over time (2 to 60 minutes). The rate of decrease in the percent fluorescence intensity of tetramer staining from Time 0 is inversely correlated with TCR affinity. Results are representative of 4 donors.
Figure 9:
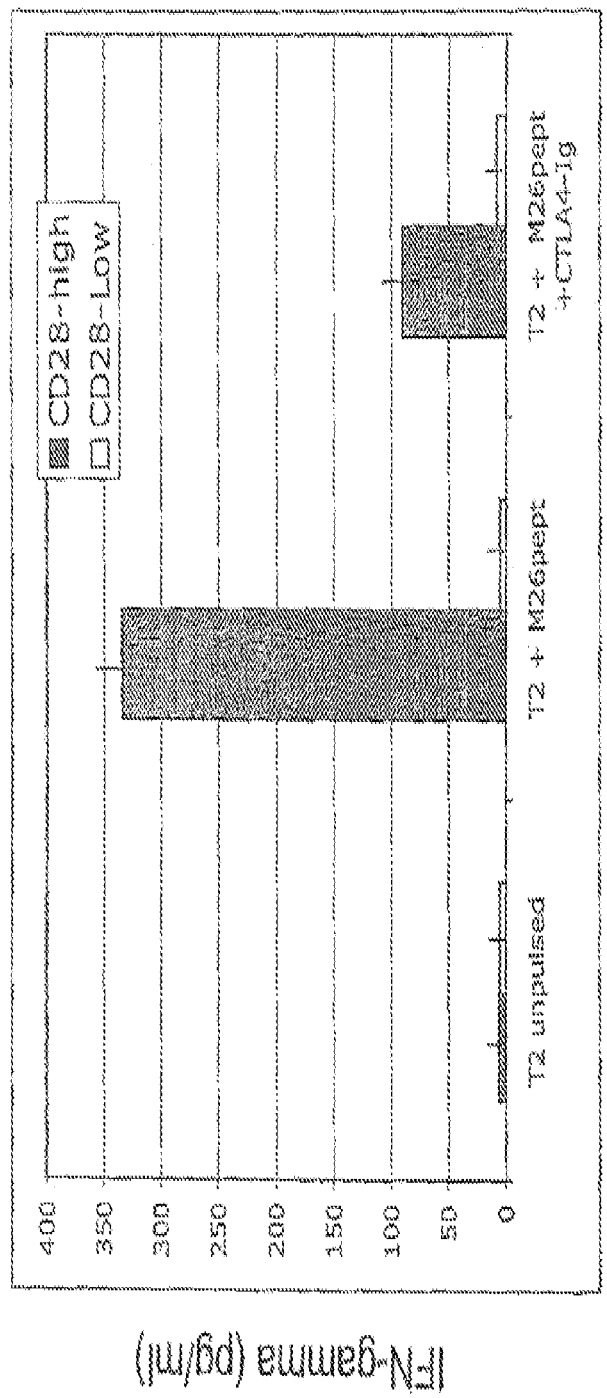
FIG. 9 illustrates IL-2 production following antigen-specific stimulation of $CD28^{hi}$ and CD28-low expressing CTL. MART-1 tetramer+ CD8+ T cells from IL-21 treated ($CD28^{hi}$) or untreated ($CD28^{low}$) cultures were sorted and co-cultivated with either unpulsed T2 cells, MART-1 (M26) peptide pulsed T2 cells alone, or with CTLA4-Ig (0.5 μg/ml) to block B7-CD28 engagement. Supernatants were collected 48 hr later and analyzed for IL-2 by ELISA. Specific induction of IL-2 production among $CD28^{hi}$ expressing MART-1-specific CTL following antigen stimulation, and inhibited by CTLA4-Ig, is observed suggesting IL-2 induction among IL-21 treated cells is CD28-dependent. Results are the mean of triplicate assays, error bars as shown.

That the increased tumor avidity is attributable to a higher affinity TCR and not other accessory factors can be demonstrated using tetramer-based TCR staining assays. Although the intensity of tetramer staining can generally be correlated with TCR affinity (Yee et al., *J. Immunol.* 162: 2227, 1999; Crawford et al., *Immunity* 8:675, 1998), a more precise definition of TCR affinity can be obtained based on the rate of tetramer dissociation, Kd, from its specific TCR ligand (Dutoit et al., *J. Immunol.* 168:675, 1990). In this assay, the Kd of the TCR-peptide-MHC interaction or TCR affinity is inversely correlated with the fraction of bound tetramer remaining over time in the presence of an excess of unlabeled tetramer. CTL clones elicited from IL-21 treated or untreated cultures were stained with M27 peptide-tetramer-PE and incubated with excess unlabelled M27-tetramer. The fraction of tetramer-bound CTL was determined by flow cytometry at specified timepoints (2 to 60 minutes). TCR/Tetramer-peptide off-rates were found to be significantly faster for clones isolated from untreated cultures compared to clones generated in IL-21 treated cultures (FIG. 7). Taken together, these results demonstrate that IL-21 treatment leads to the generation of T cells clones expressing high affinity TCR.

To demonstrate whether IL-21 mediated enrichment for high affinity T cells was due to oligoclonal expansion of a limited number of antigen-specific T cells or represented a broader effect on the T cell repertoire, TCR Vbeta expression among the cohort of high and low affinity T cell clones using a panel of anti-Vbeta antibodies was examined. For example, for patient CG, among nine high affinity T cell clones, seven expressed unique Vbeta chains (only two shared Vbeta expression) and a similarly diverse TCR repertoire was observed among the group of low affinity T cell clones in this patient (among ten different low affinity clones, only two shared the same Vbeta) suggesting that the effect of IL-21 was not due merely to the expansion of an oligoclonal population of high affinity T cell clones in vitro (FIG. 3).

Example 5

Culture of Antigen-Specific CD8 T Cells with IL-21 Sustains CD28 Expression, IFNγ and IL-2 Production CD28 is an important co-stimulatory molecule for generation of both CD4 and CD8 T cell responses. Signaling via the CD28 receptor results in increased stability of IL-2 mRNA and increased IL-2 production in both CD4 and CD8 T cells (Boise et al, *Immunity* 3:87-98, 1995; Ragheb et al, *J. Immunol.* 163:120-129, 1999). CD28 expression is lost in a subset of human CD28+ T cells after activation and this subset exhibits reduced proliferation after anti-CD3 stimulation (Azunna et al, *J. Immunol,* 150:1147-1159, 1993). CD28–CD8+ T cells are increased in the elderly and in the CD8 memory T cell pool in people with persistent viral infections, EBV and CMV (Posnett et al. *Int. Immunol.* 11:229-241, 1999). The loss of CD28 expression is most pronounced in HIV patients (Appay et al, *Nat. Med.* 8:379-385, 2002) and increases this population has been reported in patients with melanoma. Recently, it has been shown that restoring CD28 expression in CMV-specific CD8 T cells sustains IL-2 production and increased survival of antigen-specific CD8 T cells in vitro (Topp et al, *J. Exp. Med.* 198:947-955, 2005). This pathway is therefore recognized as an important pathway tor prolonged CD8 survival and function.

Figure 10:
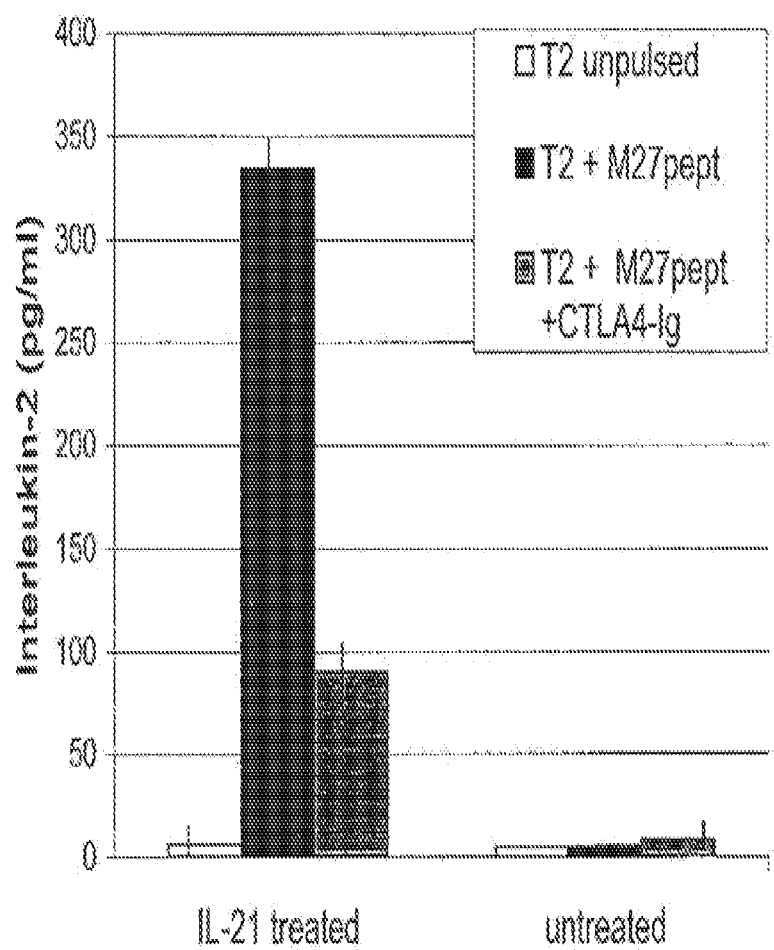
FIG. 10 illustrates IL-2 production, following antigen-specific stimulation of $CD28^{hi}$ and $CD28^{low}$ expressing CTLs. MART-1 tetramer-positive CD8 cells from IL-21 treated or untreated cultures were sorted and co-cultivated with either unpulsed T2 cells, MART-1 peptide-pulsed T2 cells alone, or with CTLA4-Ig to block B7-CD28 engagement. Supernatants were collected 48 f later and analyzed for IL-2 by ELISA. Specific induction of IL-2 production among $CD28^{hi}$ expressing MART-1 specific CTLs following antigen stimulation and inhibition by CTLA4-Ig is observed. Results are the mean of triplicate assays.

CTLs recognizing self-antigen MART-1 are present at low numbers in the peripheral blood of healthy donors and are usually characterized by a naïve phenotype (CD45RA+, CCR7+ and $CD28^{ist}$. Differentiation of this rare population in the presence of IL-21 was examined. Antigen-stimulated, untreated cells showed a CD45RO+ phenotype accompanied by loss of CCR7 and CD28 expression after a week in culture. In contrast, IL-21 treated cultures showed sustained levels of CD28 expression, even 4 weeks after primary stimulation with antigen (FIG. 10). This CD28 up-regulation was observed in both naïve healthy donors and melanoma patients for both MART-1 and gp-100 specific CTLs.

Figure 11:
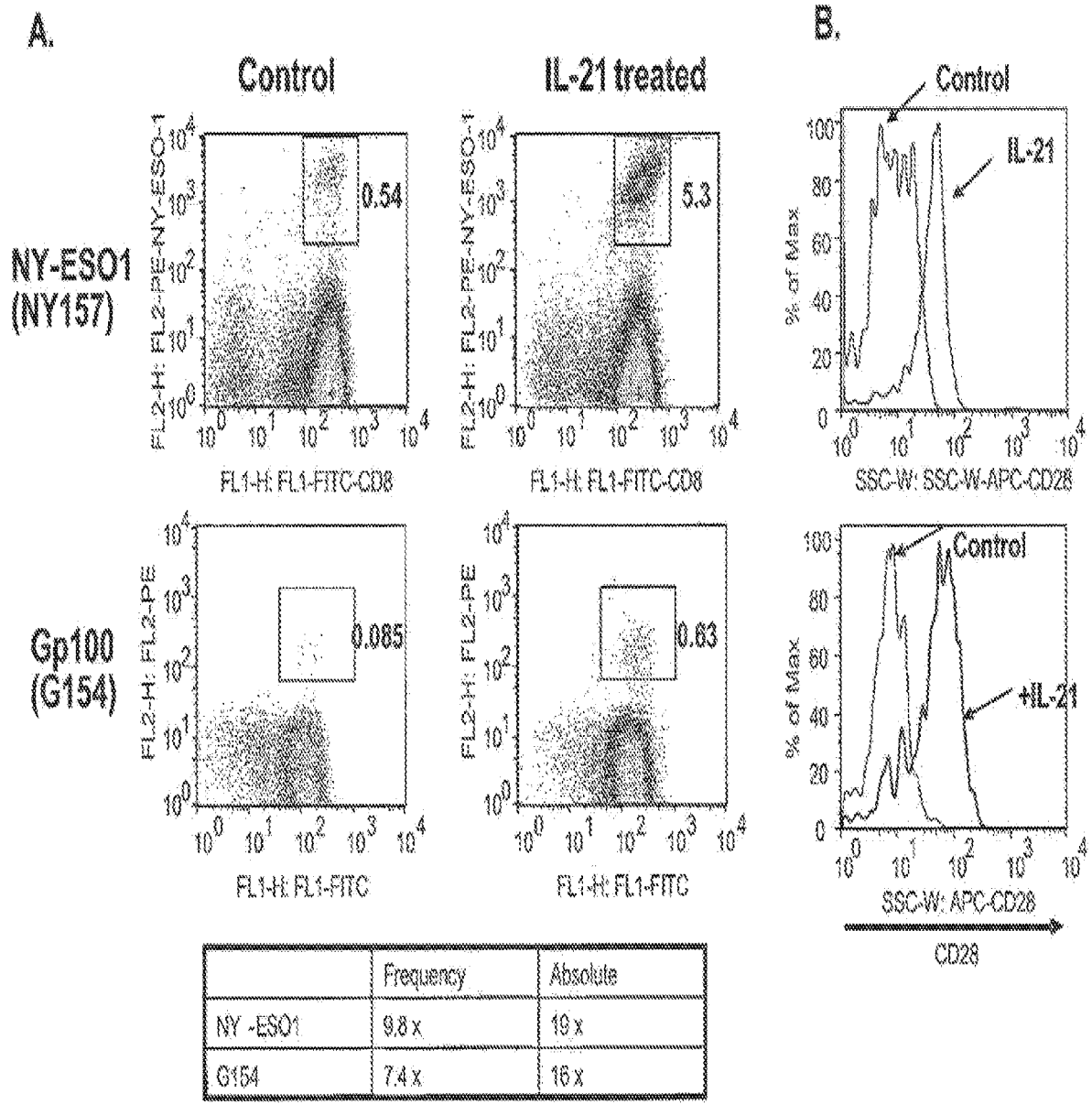
FIG. 11 illustrates that IL-21 influences the CD8 T cells response to gp100 and NY-ESO-1 antigen. CD8 T cells were stimulated both in vitro with autologous DCs pulsed with NY-ESO-1 or gp100 peptide. IL-21 was added to IL-21 treated cultures. Six days after primary in vitro stimulation cultures were analyzed for antigen specificity and surface phenotype by tetramer staining and multiparametric analysis on flow cytometry. In panel A, NY-ESO-1 and G154-specific CTL frequency are shown as percentage of all CD8 T cells next to the boxed gates. The fold increase in absolute numbers of of NY-ESO-1 specific CTLs was calculated based on numbers of cells in respective cultures and for NY-ESO-1 was found to be almost 20-fold greater among IL-21 treated cells. Panel B. Gated tetramer-positive cells from control or IL-21 treated cultures were analyzed for CD8 expression. All cells were CD45RO+, CCR7−. Histogram analysis for CD28 expression among NY-OEST-1 or gp1000-specific CTLSs was found to be significantly upregulated among IL-21 treated cultures compared to controls. There results are representative of six separate experiments from threes HLA-2+ individuals.
Figure 12:
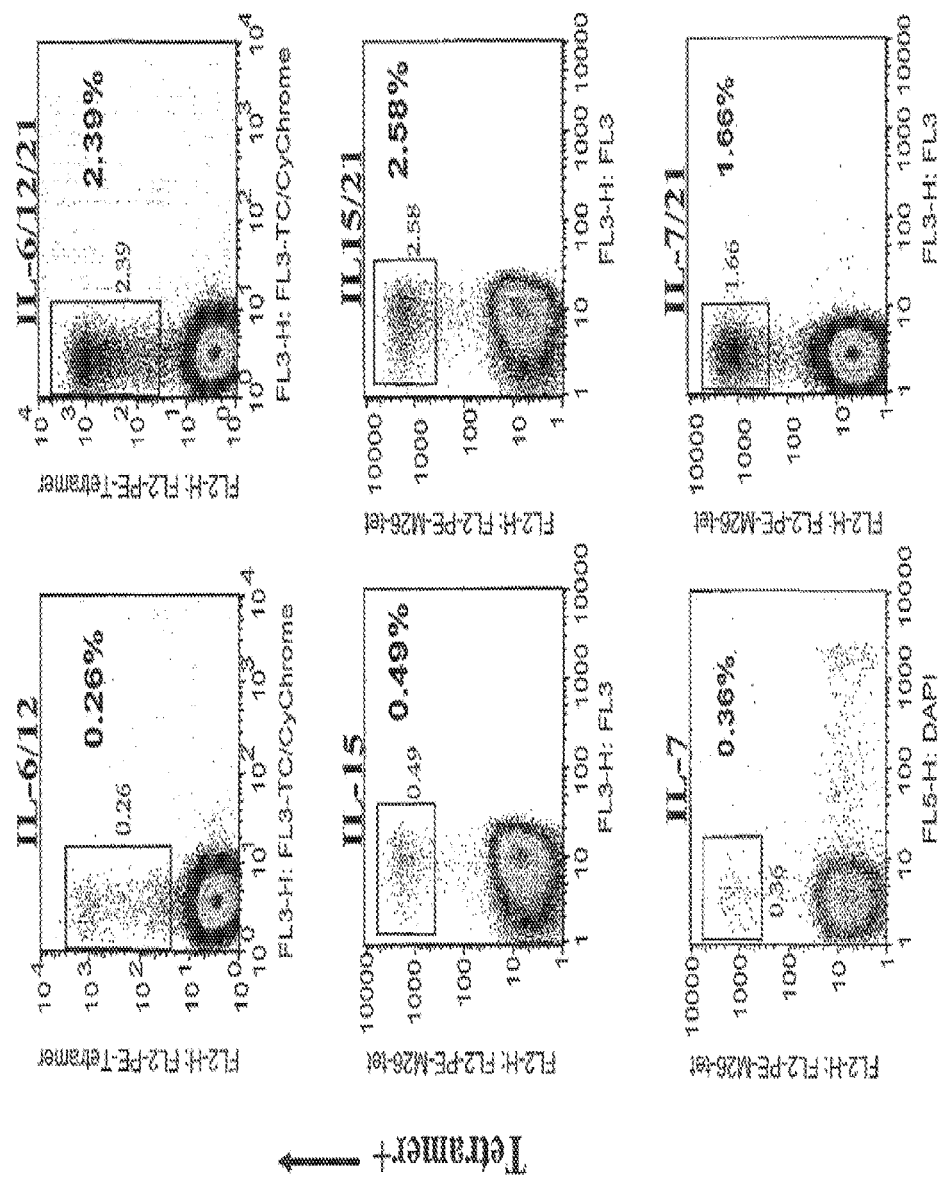
FIG. 12 illustrates that the addition of IL-21 to IL-6 and IL-12, IL-2, IL-7 or IL-15 alone significantly enhances the CD8 T cell response, compared to IL-6 and IL-12, IL-2, IL-7 or IL-15 alone.

To evaluate if upregulated CD28 expression led to a functionally competent signal, antigen-driven IL-2 and IFNγ production was analyzed in these cultures. As shown in FIG. 11, IL-2 production was significantly elevated in IL-21 treated $CD28^{hi}$ cells compared to untreated $CD28^{lo}$ expressing cells. Furthermore, IL-2 production was inhibited by addition of CTLA-4Ig, suggesting that CD28 expression was essential for IL-2 production in these cells.

These data suggest, that in vitro, IL-21 is capable of inducing a CD28 expressing memory CD8 T cell population capable of IL-2 production. This may translate to increased survival and activation of these CD8 T cells in vitro and in vivo and suggests an important role for IL -21 treatment as a monotherapy and in adoptive cell therapy for cancer and viral infections..

Example 6

IL-21 Influences the CD8+ T Cell Response to gp100 and NY-ESO-1 Antigens

To demonstrate that T cells recognize other self antigens, the influence of IL-21 on CD8+ T cells was evaluated in similar fashion using two other tumor-associated self antigens, the melanosomal antigen, gp100 (G154 peptide) and the cancer-testis antigen, NY-ESO-1 (NY157), See, Li et al., *J. Immunol.* 175:2261-2269, 2005.

CD8+ T cells were stimulated in vitro with autologous dendritic cells (DC) pulsed with NY-ESO-1 (NY157) or gp100 (G154) peptide. IL-21 (30 ng/ml) was added to IL-21-treated cultures. Six days following primary in vitro stimulation, cultures were analyzed for antigen-specificity and surface phenotype by tetramer staining and multiparametric analysis on flow cytometry.

Figure 13:
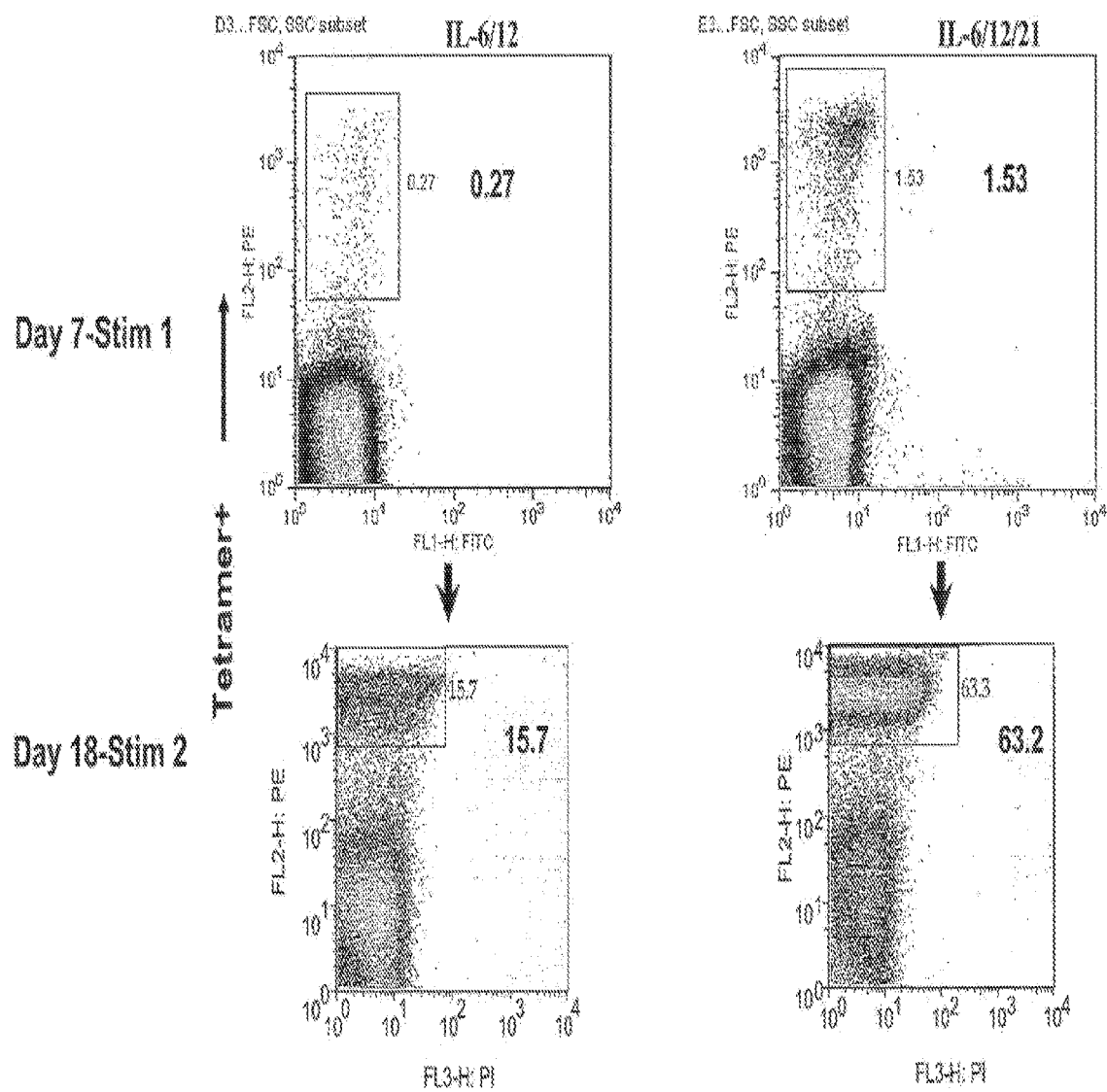
FIG. 13 illustrates that IL-21 can increase T cell frequency to levels that are high enough for expansion and adoptive transfer without further antigen-specific T cell enrichment

In FIG. 13 panel A., the NY157- and G154- specific CTL frequency are shown as % of all CD8+ T cells next to boxed gates. For example, the fold increase in NY-ESO-1-specific CTL was 9.8 fold greater among IL-21 treated cells over control (5.3%:0.54%). The fold increase in absolute numbers of NY-ESO-1-specific CTL was calculated based on numbers of cells in respective cultures and for NY-ESO-1 was found to be almost 20-fold greater among IL-21-treated cells.

In FIG. 13 panel B., gated tetramer-positive cells from control or IL-21 treated cultures were analyzed for CD28 expression. (All cells were CD45RO+, CCR7– negative). Histogram analysis for CD28 expression among NY-ESO-1 or gp100-specific CTL was found to be significantly upregulated among IL-21 treated cultures compared to control controls. These results were representative of 6 separate experiments from 3 HLA-A2+ individuals.

Example 7

Enhancement of Anti-Tumor Immunity in Melanoma Patients Receiving IL-21 Treatment After Myeloablative Therapy and Adoptive Cell Transfer Adoptive cell therapy (ACT) is based on the ex vivo selection of tumor-reactive lymphocytes, and their activation to autologus tumor-bearing boss. Tumor-specific T cells (TILs) are activated and expanded in vitro in the presence of the patient's own tumor antigens in the presence of cytokines and then transferred into the same patient followed by maintenance treatment with cytokines. In a significant number of patients, this leads to increased numbers of antigen-specific T cells in the periphery resulting in anti-tumor effects as seen by objective anti-tumor responses, IL-21 is used both as in vitro activator/expander of antigen-specific T cells and also for maintenance therapy of the T cells once transferred into the cancer patients.

All studies using human subjects receive prior approval by an Institutional Review Board at the hospital conducting clinical trials. After informed consent, peripheral blood mononuclear cells (PBMCs) are obtained and antigen-specific cytotoxic T lymphocytes (CTLs) are generated by using autologous dendritic cells pulsed with the A2-restricted peptide epitope of MART-1 (M27) or gp100 (G154) or by using a tumor cell lysate derived from a biopsy from the patients own tumor. T cells are expanded in a GMP approved reactor with appropriate cytokines (25-50 ng/ml of IL-2 or 10-50 ng/ml IrIL-21). In some cases, after three cycles of stimulation at weekly intervals, T cells are cloned by and expanded for in vitro testing. CTL clones demonstrating specific lysis of antigen-positive tumor targets in a chromium release assay are selected. Clones are expanded in 14-day cycles by using anti-CD3 antibody (OKT3, Orthoclone; Ortho Biotech, Raritan, N.J.) at 30 ng/ml, irradiated allogeneic PBMCs, at $10^6$ cells/ml, irradiated allogeneic lymphoblastoid cell lines ($2\times10^6$ cells/ml), and serial IL-2 (aldesleukin; Chiron) at 25-50 units/ml every 2-3 days. All clones are characterized as $CD3^+$, $CD4^-$, $CD8^-$ and expressed the high-affinity IL-2 receptor (CD25) after antigen stimulation.

Patients with Stage III-IV metastatic melanoma receive nonmyeloablative chemoptherapy consisting of 2 days cyclophosphamide (60 mg/kg) followed by 5 days fludarabine (25 mg/m$^2$). On the day following the final dose of of fludarabine, patients receive cell infusion of tumor-reactive lymphocytes ($10^6$-$10^{fp3}$ cells/infusion) and cytokine therapy (high dose IL-2 720,000 IU/kg iv every 8 hours or 10-30 ug/kg rIL-21 in various treatment regimens). Some patients receive a vaccination with 1 mg MART-1:26-35 (27L) or gp100:209-217 (210M) peptide in incomplete Freund's adjuvant (IFA) injected subcutaneously. Patients hematologic parameters are monitored daily. Positive therapeutic outcome can be measured using objective status protocols to assess solid tumor response. Patient response is assessed using standard radiographic studies and physical examination. See, Clinical Research Associates Manual, Southwest Oncology Group, CRAB, Seattle, Wash., Oct. 6, 1998, updated August 1999.

Presence of objective CR and/or PR responses in this trial suggest a potent role for IL-21 in anti-tumor responses in the context of adoptive cell therapy either by culturing cells in vitro with IL-21 or by maintaining patients with IL-21 after ACT.

Example 8

In Vitro Culture with IL-21 Enhances Anti-Tumor Effects in a Mouse Model of ACT

Pmel-1 transgenic mice are mice engineered to express a T cell receptor (TCR) specific for the human melanoma-specific peptide antigen gp100$_{25-33}$ (Overwijk et al., *J. Exp. Med.* 198:569-580, 2003). Splenocytes from pmel-1 transgenic mice are isolated and cultured in the presence of 1 uM human gp100$_{25-33}$ peptide and culture media containing 30 IU/ml of recombinant human IL-2 or 10-100 ng/ml murine IL-21 for 6-7 days.

Female C57Bl/6 mice (6-12 weeks old, Charles River Laboratories) are injected s.c. with 2-5×10$^5$ Bl6-F10 melanoma cells and treated 10-14 days later with i.v. adoptive transfer of in vitro cultured pmel-1 splenocytes (as specified above). Lymphopenia is induced by sublethal total body irradiation (5Gy) of tumor bearing mice on the day of transfer. Mice are then either vaccinated with 2×10$^5$ pfu recombinant fowlpox virus expressing human gp100 followed by treatment with cytokines (rhIL-2, 100 ug/dose for 6-15 doses) or treated with cytokines alone (without vaccination). Tumors are measured using calipers and volume measured using the formula tumor volume=½ (B$^2$×L) where B is the shortest diameter of the tumor and L is the longest diameter of the tumor.

Reduction in tumor growth when transferring IL-21 cultured pmel cells provide evidence of a potent role for IL-21 in in vitro activation and expansion of antigen-specific T cells for ACT.

Example 9

IL-21 Treatment In Vivo Enhances Anti-Tumor Effects in a Mouse Model of ACT

Pmel-1 transgenic mice are mice engineered to express a T cell receptor (TCR) specific for the human melanoma-specific peptide antigen gp100$_{25-33}$ (Klebanoff et al., *PNAS* 101:1969-1974, 2004) Splenocytes from pmel-1 transgenic mice are isolated and cultured in the presence of 1 uM human gp100$_{25-33}$ peptide and culture media containing 30 IU/ml of recombinant human IL-2 or 100-100 ng/ml murine IL-21 for 6-7 days.

Female C57Bl/6 mice (6-12 weeks old, Charles River Laboratories) are injected s.c. with 2-5×10$^5$ Bl6-F10 melanoma cells and treated 10-14 days later with i.v. adoptive transfer of in vitro cultured pmel-1 splenocytes (as specified above). Lymphopenia is induced by sublethal total body irradiation (5Gy) of tumor bearing mice on the day of transfer. Mice are then either vaccinated with 2×10$^5$ pfu recombinant fowlpox virus expressing human gp100 followed by treatment with cytokines (rhIL-2, 100 ug/dose or mIL-21, 20-100 µg/dose for 6-15 doses) or treated with cytokines alone (without vaccination). Tumors are measured using calipers and volume measured using the formula tumor volume=½ (B$^2$×L) where B is the shortest diameter of the tumor and L is the longest diameter of the tumor.

Reduction in tumor growth after IL-21 treatment in vivo demonstrates a role for IL-21 in maintenance and activation of tumor-specific T cells a after ACT.

From the foregoing, it will be appreciated that, although specific embodiments of the invention have been described herein for purposes of illustration, various modifications may be made without deviating from the spirit and scope of the invention. Accordingly, the invention is not limited except as by the appended claims.

What is claimed is:

1. A method of preparing a T cell population comprising:
   obtaining the T cell population from PBMCs;
   activating the obtained T cell population,
   transducing the activated T cell population with a viral vector comprising a nucleic acid encoding a protein,
   expanding the transduced T cell population, and
   wherein the activating, transducing, and expanding are performed in the presence of IL-21.

2. The method of claim 1, wherein the PBMCs are obtained from a patient or a healthy donor.

3. The method of claim 1, wherein the activating, transducing, and expanding are further performed in the presence of at least one cytokine selected from IL2, IL-12, and IL15.

4. The method of claim 1, wherein the protein is a T cell receptor.

5. The method of claim 1, further comprising restimulating the expanded transduced T cell population.

6. The method of claim 5, wherein the restimulating is performed in the presence of a feeder cell and an anti-CD3 antibody.

7. The method of claim 6, wherein the feeder cell is an irradiated allogenic feeder cell.

8. The method of claim 7, wherein the feeder cell comprises a PBL and a LCL.

9. The method of claim 8, further comprising culturing the restimulated cells in the presence of IL-2.

* * * * *